US009902770B2

(12) United States Patent
Chi et al.

(10) Patent No.: US 9,902,770 B2
(45) Date of Patent: Feb. 27, 2018

(54) INTERFERON ALPHA AND OMEGA ANTIBODY ANTAGONISTS

(71) Applicant: Janssen Biotech, Inc., Horsham, PA (US)

(72) Inventors: Ellen Chi, San Diego, CA (US); Judith Connor, San Diego, CA (US); Chichi Huang, Spring House, PA (US); Jarrat Jordan, Spring House, PA (US); Xiefan Lin-Schmidt, San Diego, CA (US); Jinquan Luo, Spring House, PA (US); Lu Lu, San Diego, CA (US); Christian Martinez, San Diego, CA (US); Galina Obmolova, Spring House, PA (US); Ronald Swanson, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 230 days.

(21) Appl. No.: 14/208,861

(22) Filed: Mar. 13, 2014

(65) Prior Publication Data

US 2014/0271648 A1    Sep. 18, 2014

Related U.S. Application Data

(60) Provisional application No. 61/788,302, filed on Mar. 15, 2013.

(51) Int. Cl.
| | |
|---|---|
| *C07K 16/24* | (2006.01) |
| *C07K 16/46* | (2006.01) |
| *A61K 39/395* | (2006.01) |

(52) U.S. Cl.
CPC ........ *C07K 16/249* (2013.01); *C07K 2317/21* (2013.01); *C07K 2317/31* (2013.01); *C07K 2317/33* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,223,409 A | 6/1993 | Ladner et al. | |
| 5,317,089 A | 5/1994 | Adolf | |
| 5,770,429 A | 6/1998 | Lonberg et al. | |
| 5,869,620 A | 2/1999 | Whitlow et al. | |
| 5,885,793 A | 3/1999 | Griffiths et al. | |
| 5,932,448 A | 8/1999 | Tso et al. | |
| 5,939,598 A | 8/1999 | Kucherlapati et al. | |
| 5,969,108 A | 10/1999 | McCafferty et al. | |
| 6,833,441 B2 | 12/2004 | Wang et al. | |
| 7,041,870 B2 | 5/2006 | Tomizuka et al. | |
| 7,087,726 B2 | 8/2006 | Chuntharapai et al. | |
| 7,695,936 B2 | 4/2010 | Carter et al. | |
| 8,025,882 B2 | 9/2011 | Witte et al. | |
| 2005/0019306 A1 | 1/2005 | Horvath et al. | |
| 2007/0014724 A1 | 1/2007 | Witte et al. | |
| 2007/0287170 A1 | 12/2007 | Davis et al. | |
| 2008/0160030 A1 | 7/2008 | Banchereau et al. | |
| 2009/0118127 A1 | 5/2009 | Raghunathan | |
| 2009/0182127 A1 | 7/2009 | Kjaergaard et al. | |
| 2009/0186027 A1 | 7/2009 | Solomon et al. | |
| 2010/0015133 A1 | 1/2010 | Igawa et al. | |
| 2010/0021477 A1 | 1/2010 | Tsui et al. | |
| 2010/0057153 A1 | 3/2010 | Ballis | |
| 2010/0143369 A1* | 6/2010 | Cardarelli | C07K 16/2866 424/142.1 |
| 2010/0286374 A1 | 11/2010 | Kannan et al. | |
| 2011/0123532 A1 | 5/2011 | Gurney et al. | |
| 2011/0206672 A1 | 8/2011 | Little et al. | |
| 2011/0213125 A1* | 9/2011 | Svensson | C07K 16/249 530/387.1 |
| 2012/0108795 A1 | 5/2012 | Kehoe et al. | |
| 2012/0114667 A1 | 5/2012 | Eberlein et al. | |
| 2012/0149876 A1 | 6/2012 | Von Kreudenstein et al. | |

FOREIGN PATENT DOCUMENTS

| | | |
|---|---|---|
| EP | 0 490 233 A1 | 3/1987 |
| WO | WO 88/01649 A1 | 3/1988 |
| WO | WO 92/01047 A1 | 1/1992 |
| WO | WO 94/13804 A1 | 6/1994 |
| WO | WO 95/15388 A1 | 6/1995 |
| WO | WO 97/14719 A1 | 4/1997 |
| WO | WO 98/44001 A1 | 10/1998 |
| WO | WO 99/57150 A2 | 11/1999 |
| WO | WO 2004/111233 A1 | 12/2004 |
| WO | WO 2008/119353 A1 | 10/2008 |
| WO | WO 2009/085462 A1 | 7/2009 |

(Continued)

OTHER PUBLICATIONS

Kolchanov, 1988, Journal of Molecular Evolution, vol. 27, pp. 154-162.*
Pasquo, 2012, PLoS ONE, vol. 7, Issue 2, e32555.*
Bork, 2000, Genome Research 10:398-400.*
Bork et al., 1996, Trends in Genetics 12:425-427.*
Xuejun et al. (1999), Science in China (series C), vol. 42, No. 2, pp. 191-201.*
Thomas et al. (2011), Cell, Vo. 146, pp. 621-632.*
Adams, et al., "Recent developments in the PHENIX software for automated crystallographic structure determination," Journal of Synchrotron Radiation, 11: 53-55 (2004).
Adolf, et al., "Purification and Characterization of Natural Human Interferon ω1, "The Journal of Biological Chemistry, 265(16): 9290-9295 (1990).
Adolf, et al., "Antigenic Structure of Human Interferon ω1 (Interferon $α_{II}1$): Comparison with Other Human Interferons," Journal of General Virology, 68: 1669-1676 (1987).
GR Adolf, "Human interferon omega—a review," Multiple Sclerosis, 1: S44-S47 (1995).

(Continued)

*Primary Examiner* — Christine J Saoud
*Assistant Examiner* — Jegatheesan Seharaseyon
(74) *Attorney, Agent, or Firm* — Eric Dichter

(57) ABSTRACT

Broadly neutralizing interferon-α and interferon-ω antibody antagonists, polynucleotides encoding the antibodies or fragments, and methods of making and using the foregoing are useful in the treatment of diseases associated with increased production of IFNα and IFNω.

15 Claims, 9 Drawing Sheets

(56) References Cited

FOREIGN PATENT DOCUMENTS

Figure 1A:
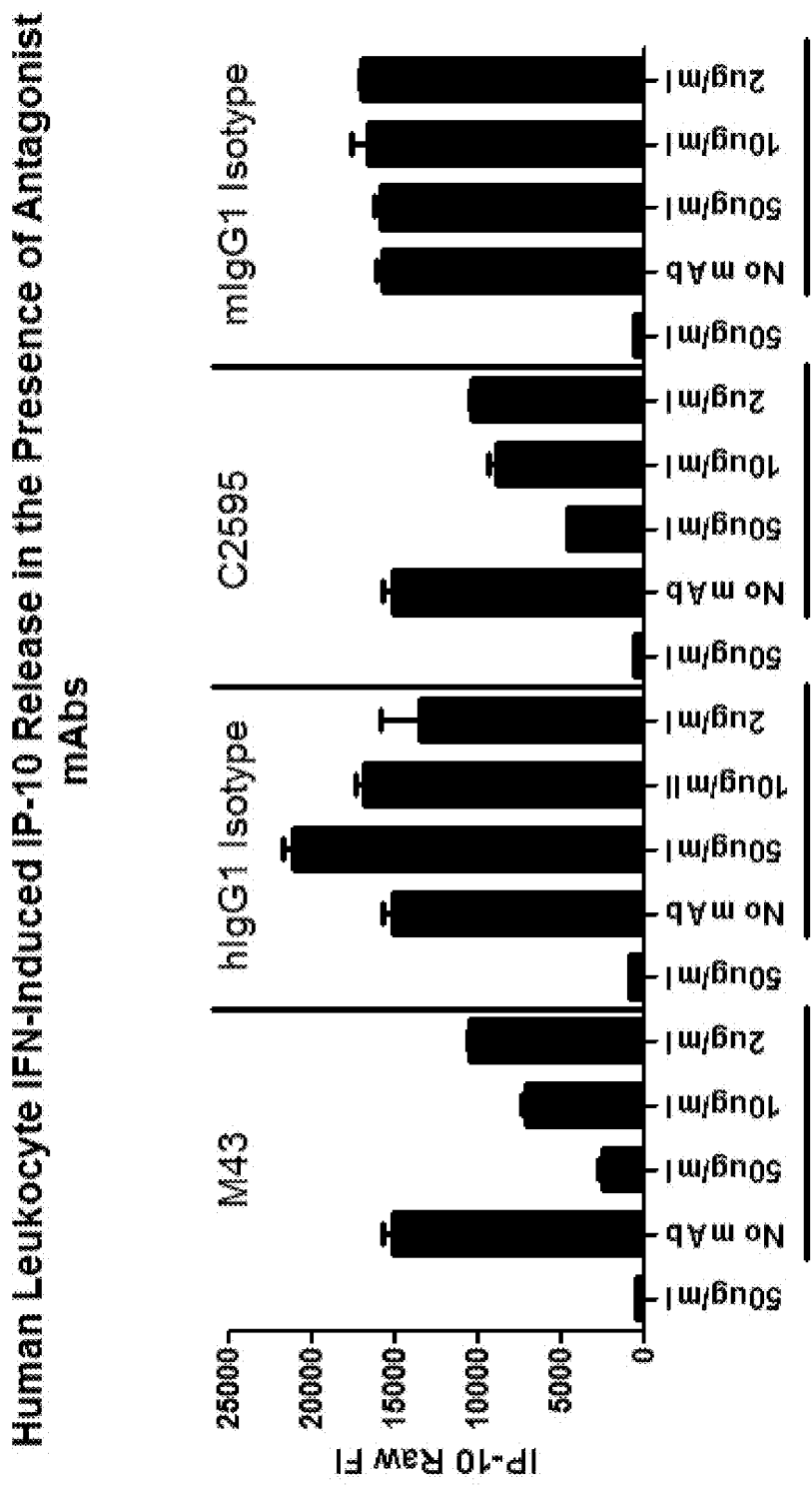

| WO | WO 2009/134776 A2 | 11/2009 |
|---|---|---|
| WO | WO 2009/135861 A2 | 11/2009 |
| WO | WO 2011/035460 A1 | 3/2011 |
| WO | WO 2011/131746 A2 | 10/2011 |
| WO | WO 2011/143545 A1 | 11/2011 |
| WO | WO 2012/022811 A1 | 2/2012 |

OTHER PUBLICATIONS

Al-Lazikani, et al., "Standard Conformation for the Canonical Structures of Immunoglobulins," Journal of Molecular Biology, 273: 927-948 (1997).

Almagro, et al., "Identification of differences in the specificity-determining residues of antibodies that recognize antigens of different size: implications for the rational design of antibody repertoires," Journal of molecular Recognition, 17: 132-143 (2004).

Baechler, et al., "Interferon-inducible gene expression signature in peripheral blood cells of patients with severe lupus," Proceedings of the National Academy of Science, 100(5): 2610-2615 (2003).

Bedu-Addo, et al., "Use of Biophysical Characterization in Preformulation Development of a Heavy-Chain Fragment of Botulinum Serotype B: Evaluation of Suitable Purification Process Conditions," Pharmaceutical Research, 21(8): 1353-1361 (2004).

Benoit, et al., "A monoclonal antibody to recombinant human IFN-alpha receptor inhibits biologic activity of several species of human IFN-alpha, IFN-beta, and IFN-omega. Detection of heretogeneity of the cellular type I IFN receptor," The Journal of Immunology, 150: 707-716 (1993).

Bennett, et al., "Interferon and Granulopoiesis Signatures in Systemic Lupus Erythematosus Blood," The Journal of Experimental Medicine, 197(6): 711-723 (2003).

Biggioggero, et al., "Type I interferon therapy and its role in autoimmunity," Autoimmunity, 53(3): 248-254 (2010).

Burdick, et al., "Type I IFNs and their role in the development of autoimmune diseases," Expert Opinion on Drug Safety, 8(4):459-472 (2009).

Chothia, et al., "Canonical Structures for the Hypervariable Regions of Immunoglobulins," Journal of Molecular Biology, 196: 901-917 (1987).

Dall'Era, et al., "Type I interferon correlates with serological and clinical manifestations of SLE," Annals of the Rheumatic Diseases, 64: 1692-1697 (2005).

Deonarian, et al., "Protective Role for Interferon-β in Coxsackievirus B3 Infection," Circulation, 110: 3540-3543 (2004).

Deonarain, et al., Impaired Antiviral Response and Alpha/Beta Interferon Induction in Mice Lacking Beta Interferon, Journal of Virology, 74(7): 3404-3409 (2000).

Emsley, et al., "Coot: model building tools for molecular graphics," Acta Crystallographica, D60: 2126-2132 (2004).

Fishwild, et al., "High-avidity human IgGκ monoclonal antibodies from a novel strain of minilocus transgenic mice," Nature Biotechnology, 14: 845-851 (1996).

Gerlach, et al., "Effects of Type I Interferons on Friend Retrovirus Infection," Journal of Virology, 80(7): 3438-3444 (2006).

Gibson, et al., "Plasmacytoid dendritic cells produce cytokines and mature in response to the TLR7 agonists, imiquimod and resiquimod," Cellular Immunology, 218: 74-86 (2002).

Gupta, et al., Development of a Multidose Formulation for a Humanized Monclonal Antibody Using Experimental Design Techniques, AAPS PharmSci, 5(2): 1-9 (2003).

Han, et al., "*Analysis of gene expression profiles in human systemic lupus erythematosus using oligonucleotide microarray*," Genes and Immunity, 4: 177-186 (2003).

John Hodgson, "Making Monoclonals in Microbes," Biotechnology, 9: 421-425 (1991).

Hooks, et al., "Immune Interferon in the circulation of Patients with Autoimmune Disease," New England Journal of Medicine, 301: 5-8 (1979).

Hua, et al., "Functional Assay of type I Interferon in Systemic Lupus Erythematosus Plasma and Association with Anti-RNA Binding Protein Autoantibodies," Arthritis & Rheumatism, 54(6): 1906-1916 (2006).

Wolfgang Kabsch, "XDS," Acta Crystallography, D66: 125-132 (2010).

Kalunian, et al., "Efficacy and Safety of Rontalizumab (Anti-Interferon Alpha) in SLE Subjects with Restricted Immunosuppressant Use: Results of a Randomized, Double-Blind, Placebo-Controlled Phase 2 Study." Arthritis & Rheumatism, 64: Abstract Supplement, Nov. 2012.

Karageorgas, et al., "Activation of type I Interferon Pathway in Systemic Lupus Erythematosus: Association with Distinct Clinical Phonotypes," Journal of Biomedicine and Biotechnol , 2011: 1-13 (2011).

Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2000).

Knight, et al., "Pharmacodynamic enhancement of the anti-platelet antibody Fab abciximab by site-specific pegylation," Platelets, 15(7): 409-418 (2004).

Koerner, et al., "Protectie Role of Beta Interferon in Host Defense against Influenza A Virus," Journal of Virology, 81(4): 2025-2030 (2007).

Kohler, et al., Continuous cultures of fused cells secreting antibody of Predefined specificity, Nature, 256: 495-497 (1975).

Krebs, et al., "High-throughput generation and engineering of recombinant human antibodies," Journal of Immunological Methods, 254: 67-84 (2001).

Kubes, et al., "Cross-Species Antiviral and Antiproliferative Activity of Human Interferon-ω," Journal of Interferon Research, 14: 57-59 (1994).

Lazear, et al., "Beta Interferon Controls West Nile Virus Infection and Pathogenesis in Mice," Journal of Virology, 85(14): 7186-7194 (2011).

Lafleur, et al., "Interferon-κ, a Novel Type I Interferon Expressed in Human Keratinocytes," The Journal of Biological Chemistry, 276(43): 39765-39771 (2001).

Lefranc, et al., "IMGT unique numbering for immunoglobulin and T cell receptor variable domains and Ig superfamily V-like domains," Development and Comparative Immunology, 27: 55-77 (2003).

Leong, et al., "Adapting Pharmacokinetic Properties of a Humanized Anti-Interleukin-8 Antibody for Therapeutic Applications Using Site-Specific Pegylation," Cytokine, 16(3): 106-119 (2001).

Lonberg, et al., Antigen-specific human antibodies from mice comprising four distinct genetic modifications, Nature, 368: 856-859 (1994).

Luo, et al., "Coevolution of Antibody Stability and Vκ CDR-L3 Canonical Structure," Journal of Molecular Biology, 402: 708-719 (2010).

Maa, et al., "Aggregation of recombinant human growth hormone induced by phenolic compounds," International Journal of Pharmacies, 140: 155-168 (1996).

Mendez, et al., "Functional transplant of megabase human immunoglobulin loci recapitulates human antibody response in mice," Nature Genetics, 15: 146-156 (1997).

Merrill, et al., "Safety profile and clinical activity of sifalimumab, a fully human anti-interferon a monoclonal antibody, in systemic lupus erythematosus: a phase I, multicentry, double-blind randomized study," Annals of the Rheumatic Disease, 70: 1905-1913 (2011).

Murshudov, et al., "Refinement of Macromolecular Structures by the Maximum-Likelihood Method," Acta Crystallographica Section D, D53: 240-255 (1997).

Niewold, et al., "*High serum IFN-α activity is a heritable risk factor for systemic lupus erythematosus*," Genes and Immunity, 8: 492-502 (2007).

Obmolova, et al., "Promoting crystallization of antibody-antigen complexes via microseed matrix screening," Acta Crystallographia Section D, D66: 927-933 (2010).

(56) References Cited

OTHER PUBLICATIONS

Perry, eta l., "Murine Models of Systemic Lupus Erythematosus," Journal of Biomedicine and Biotechnology, 2011: 1-19 (2011).

Preble, et al., Systemic Lupus Erythematosus: Presence in Human Serum of an Unusual Acid-Labile Leukocyte Interferon, Science, 216: 429-431 (1982).

Queen, et al., "A humanized antibody that binds to the interleukin 2 receptor," Proceedings of the National Academy of Science USA, 86: 10029-10033 (1989).

Radhakrishnan, et al., "Zinc mediated dimer of human interferon-$\alpha_{2b}$ revealed by X-ray crystallography," Structure, 4: 1453-1463 (1996).

Randy J. Read, "Pushing the boundaries of molecular replacement with maximum likelihood," Acta Crystallographica Section D, D57: 1373-1382 (2001).

Remmele, et al., "Interkeukin-1 Receptor (IL-1R) Liquid Formulation Development Using Differential Scanning Calorimetry," Pharmaceutical Research, 15(2): 200-208 (1998).

Remmele, et al., "Differential Scanning Calorimetry. A Practical Tool for Elucidating Stability of Liquid Biopharmaceuticals," Biopharmaceuticals, 13: 36-46 (2000).

Ritterhouse, et al., "B Lymphocyte Stimulator Levels in Systemic Lupus Erythematosus," Arthritis & Rheumatism, 63(12): 3931-3941 (2011).

Roberts, et al., "The Evolution of the Type I Interferons," Journal of Interferon and Cytokine Research, 18: 805-816 (1998).

Shi, et al., "De Novo Selection of High-Affinity Antibodies from Synthetic Fab Libraries Displayed in Phage as pIX Fusion Proteins," Journal of Molecular Biology, 397: 385-396 (2010).

Slavikova, et al., "Incidence of Autoantibodies Against type I and Type II Interferons in a Cohort of Systemic Lupus Erythematosus Patients in Slovakia," Journal of Interferon & Cytokine Research, 23: 143-147 (2003).

Stanfield, et al., "Antibody Elbow Angles are Influenced by their Light Chain Class," Journal of Molecular Biology, 357: 1566-1574 (2006).

William R. Strohl, "Optimization of Fc-mediated effector functions of monoclonal antibodies," Current Opinion in Biotechnology, 20: 685-691 (2009).

Terenzi, et al., "Distinct Induction Patterns and Functions of Two Closely Related Interferon-inducibly Human Genes, ISG54 and ISG56," The Journal of Biological Chemistry, 281(45): 34064-34071 (2006).

Thomas, et al, "Structural Linkage between Ligand Discrimination and Receptor Activation by Type I Interferons," Cell, 621-632 (2011).

Tiefenthaler, et al., "A Comparison of the Antiproliferative Properties of Recombinant Human IFN-$\alpha$2 and IFN-$\omega$ in Human Bone Marrow Culture," Journal of Interferon and cytokine Research, 17: 327-329 (1997).

Van Pesch, et al., "Characterization of the Murine Alpha Interferon Gene Family," Journal of Virology, 78(15): 8219-8228 (2004).

Wang, et al., "Pharmacogenomics and Translations Simulations to Bridge Indications for an Anti-Interferon-$\alpha$ Receptor Antibody," Clinical Pharmacology & therapeutics, 93(6): 483-492 (2013).

Weissmann, et al., "The Interferon Genes: Types, Effects, and Properties of Interferons," Progress in Nucleic Acid Research and Molecular Biology, 33: 251-300 (1986).

Worn, et al., "Stability Engineering of Antibody Single-chain Fv Fragments," Journal of Molecular Biology, 305: 989-1010 (2001).

Yang, et al., "Tailoring structure-function and pharmacokinetic properties of single-chain Fv proteins by site-specific PEGylation," Protein Engineering, 16(10): 761-770 (2003).

Yao, et al., "Neutralization of Interferon-$\alpha$/$\beta$-Inducible Genes and Downstream Effect in a Phase I Trial of an Anti-Interferon-$\alpha$ Monoclonal Antibody in Systemic Lupus Erythematosus," Arthritis & Rheumatism, 60(6): 1785-1796 (2009).

Yasui, et al., "Effects of substitutions of amino acids on the thermal stability of the Fv fragments of antibodies," FEBS Letters, 353: 143-146 (1994).

Zagury, et al., "IFN$\alpha$ kinoid vaccine-induced neutralizing antibodies prevent clinical manifestations in a lupus flare murine model," Proceedings of the National Academy of Science, 106(13): 5294-5299 (2009).

Zhang, et al., "Mechanism for Benzyl Alcohol-Induced Aggregation of Recombinant Human Interleukin-1 receptor Antagonist in Aqueous Solution," Journal of Pharmaceutical Sciences, 93(12): 3076-3089 (2004).

Supplemental European Search Report dated Oct. 11, 2016 and dated Oct. 21, 2016.

Gunther R. Adolf, "Monoclonal Antibodies and Enzyme Immunoassays Specific for Human Interferon (IFN)$\omega$1: Evidence the IFN-$\omega$1 Is a Component of Human leukocyte IFN," Virology, 175: 410-417 (1990).

PCT International Search Report dated Jul. 8, 2014.

\* cited by examiner

SEQUENCE LISTING

<160> NUMBER OF SEQ ID NOS: 40

<210> SEQ ID NO 1
<211> LENGTH: 172
<212> TYPE: PRT
<213> ORGANISM: Homo Sapiens

<400> SEQUENCE: 1

Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
                20                  25                  30

Arg Arg Asp Phe Arg Phe Pro Gln Glu Met Val Lys Gly Ser Gln Leu
            35                  40                  45

Gln Lys Ala His Val Met Ser Val Leu His Glu Met Leu Gln Gln Ile
        50                  55                  60

```
Phe Ser Leu Phe His Thr Glu Arg Ser Ser Ala Ala Trp Asn Met Thr
 65                  70                  75                  80

Leu Leu Asp Gln Leu His Thr Gly Leu His Gln Gln Leu Gln His Leu
                 85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
            115                 120                 125

Val Tyr Leu Lys Glu Lys Lys Tyr Ser Asp Cys Ala Trp Glu Val Val
            130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser
                165                 170

<210> SEQ ID NO 2
<211> LENGTH: 172
<212> TYPE: PRT
<213> ORGANISM: Homo sapiens

<400> SEQUENCE: 2

Cys Asp Leu Pro Gln Asn His Gly Leu Leu Ser Arg Asn Thr Leu Val
 1                5                  10                  15

Leu Leu His Gln Met Arg Arg Ile Ser Pro Phe Leu Cys Leu Lys Asp
                 20                  25                  30

Arg Arg Asp Phe Arg Phe Pro Gln Glu Met Val Lys Gly Ser Gln Leu
             35                  40                  45

Gln Lys Ala His Val Met Ser Val Leu His Glu Met Leu Gln Gln Ile
     50                  55                  60

Phe Ser Leu Phe His Thr Glu Arg Ser Ser Ala Ala Trp Asn Met Glu
 65                  70                  75                  80

Leu Leu Asp Gln Leu His Thr Gly Leu His Gln Gln Leu Gln His Leu
                 85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
            115                 120                 125

Val Tyr Leu Lys Glu Lys Lys Tyr Ser Asp Cys Ala Trp Glu Val Val
            130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser
                165                 170

<210> SEQ ID NO 3
<211> LENGTH: 177
<212> TYPE: PRT
<213> ORGANISM: Pan troglodytes

<400> SEQUENCE: 3

Cys Asp Leu Pro Gln Asn His Gly Leu Leu Ser Arg Asn Thr Leu Val
 1                5                  10                  15

Leu Leu His Gln Met Arg Arg Ile Ser Pro Phe Leu Cys Leu Lys Asp
                 20                  25                  30

Arg Arg Asp Phe Arg Phe Pro Gln Glu Met Val Lys Gly Ser Gln Leu
             35                  40                  45
```

```
Gln Lys Ala Gln Val Met Ser Val Leu His Glu Met Leu Gln Gln Ile
         50                  55                  60

Phe Ser Leu Phe His Thr Glu Arg Ser Ser Ala Ala Trp Asn Met Thr
 65                  70                  75                  80

Leu Leu Asp Gln Leu His Thr Gly Leu His Gln Gln Leu Gln His Leu
                 85                  90                  95

Glu Thr Cys Leu Leu Gln Val Met Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser Arg Asn Asp Ser
                165                 170                 175

His

<210> SEQ ID NO 4
<211> LENGTH: 172
<212> TYPE: PRT
<213> ORGANISM: Macaca fascicularis

<400> SEQUENCE: 4

Cys Asp Leu Pro Gln Asn His Gly Leu Leu Ser Arg Asn Thr Leu Val
  1               5                  10                  15

Leu Leu His Gln Met Arg Arg Ile Ser Pro Phe Leu Cys Leu Lys Asp
                 20                  25                  30

Arg Arg Asp Phe Arg Phe Pro Gln Glu Met Val Glu Gly Ser Gln Leu
             35                  40                  45

Gln Lys Ala Gln Val Met Ser Val Leu His Glu Met Leu Gln Gln Ile
         50                  55                  60

Phe Ser Leu Phe His Thr Glu His Ser Ser Ala Ala Trp Asn Thr Thr
 65                  70                  75                  80

Leu Leu Asp His Leu His Thr Gly Leu His Arg Gln Leu Glu His Leu
                 85                  90                  95

Glu Thr Cys Leu Val Gln Val Met Arg Glu Gly Glu Ser Ala Gly Ala
            100                 105                 110

Ile Arg Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Val Val Val
130                 135                 140

Arg Met Glu Ile Met Lys Ser Leu Phe Leu Ser Thr Asn Met Gln Glu
145                 150                 155                 160

Arg Leu Lys Ser Lys Asp Gly Asp Leu Gly Ser Ser
                165                 170

<210> SEQ ID NO 5
<211> LENGTH: 165
<212> TYPE: PRT
<213> ORGANISM: Homo sapiens

<400> SEQUENCE: 5

Cys Asp Leu Pro Gln Thr His Ser Leu Gly Ser Arg Arg Thr Leu Met
  1               5                  10                  15

Leu Leu Ala Gln Met Arg Lys Ile Ser Leu Phe Ser Cys Leu Lys Asp
```

```
                    20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
        50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 6
<211> LENGTH: 166
<212> TYPE: PRT
<213> ORGANISM: Homo sapiens

<400> SEQUENCE: 6

Cys Asp Leu Pro Gln Thr His Ser Leu Gly Asn Arg Arg Ala Leu Ile
 1               5                  10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
 65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
130                 135                 140

Arg Ala Glu Ile Met Arg Ser Phe Ser Leu Ser Ile Asn Leu Gln Lys
145                 150                 155                 160

Arg Leu Lys Ser Lys Glu
                165

<210> SEQ ID NO 7
<211> LENGTH: 166
<212> TYPE: PRT
<213> ORGANISM: Homo sapiens

<400> SEQUENCE: 7

Cys Asp Leu Pro Gln Thr His Ser Leu Gly Asn Arg Arg Ala Leu Ile
```

```
              1               5                  10                 15
Leu Leu Gly Gln Met Gly Arg Ile Ser Pro Phe Ser Cys Leu Lys Asp
                20                  25                 30

Arg His Asp Phe Arg Ile Pro Gln Glu Glu Phe Asp Gly Asn Gln Phe
                35                  40                 45

Gln Lys Ala Gln Ala Ile Ser Val Leu His Glu Met Ile Gln Gln Thr
            50                  55                 60

Phe Asn Leu Phe Ser Thr Glu Asp Ser Ser Ala Ala Trp Glu Gln Ser
65                  70                  75                 80

Leu Leu Glu Lys Phe Ser Thr Glu Leu Tyr Gln Gln Leu Asn Asp Leu
                85                  90                 95

Glu Ala Cys Val Ile Gln Glu Val Gly Val Glu Glu Thr Pro Leu Met
                100                 105                110

Asn Glu Asp Ser Ile Leu Ala Val Arg Lys Tyr Phe Gln Arg Ile Thr
                115                 120                125

Leu Tyr Leu Ile Glu Arg Lys Tyr Ser Pro Cys Ala Trp Glu Val Val
            130                 135                 140

Arg Ala Glu Ile Met Arg Ser Leu Ser Phe Ser Thr Asn Leu Gln Lys
145                 150                 155                160

Arg Leu Arg Arg Lys Asp
                165

<210> SEQ ID NO 8
<211> LENGTH: 166
<212> TYPE: PRT
<213> ORGANISM: Homo sapiens

<400> SEQUENCE: 8

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
                20                  25                 30

Arg His Asp Phe Gly Phe Pro Gln Glu Glu Phe Asp Gly Asn Gln Phe
                35                  40                 45

Gln Lys Ala Pro Ala Ile Ser Val Leu His Glu Leu Ile Gln Gln Ile
            50                  55                 60

Phe Asn Leu Phe Thr Thr Lys Asp Ser Ser Ala Ala Trp Asp Glu Asp
65                  70                  75                 80

Leu Leu Asp Lys Phe Cys Thr Glu Leu Tyr Gln Gln Leu Asn Asp Leu
                85                  90                 95

Glu Ala Cys Val Met Gln Glu Glu Arg Val Gly Glu Thr Pro Leu Met
                100                 105                110

Asn Val Asp Ser Ile Leu Ala Val Lys Lys Tyr Phe Arg Arg Ile Thr
                115                 120                125

Leu Tyr Leu Thr Glu Lys Lys Tyr Ser Pro Cys Ala Trp Glu Val Val
            130                 135                 140

Arg Ala Glu Ile Met Arg Ser Leu Ser Leu Ser Thr Asn Leu Gln Glu
145                 150                 155                160

Arg Leu Arg Arg Lys Glu
                165

<210> SEQ ID NO 9
<211> LENGTH: 166
<212> TYPE: PRT
<213> ORGANISM: Homo sapiens
```

```
<400> SEQUENCE: 9

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Met
                85                  90                  95

Glu Ala Cys Val Ile Gln Glu Val Gly Val Glu Thr Pro Leu Met
            100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 10
<211> LENGTH: 166
<212> TYPE: PRT
<213> ORGANISM: Homo sapiens

<400> SEQUENCE: 10

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Met Met Gln Glu Val Gly Val Glu Asp Thr Pro Leu Met
            100                 105                 110

Asn Val Asp Ser Ile Leu Thr Val Arg Lys Tyr Phe Gln Arg Ile Thr
            115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Ala Asn Leu Gln Glu
145                 150                 155                 160

Arg Leu Arg Arg Lys Glu
                165

<210> SEQ ID NO 11
<211> LENGTH: 166
```

-continued

```
<212> TYPE: PRT
<213> ORGANISM: Homo sapiens

<400> SEQUENCE: 11

Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
                20                  25                  30

Arg His Asp Phe Glu Phe Pro Gln Glu Glu Phe Asp Gly Asn Gln Phe
            35                  40                  45

Gln Lys Ala Gln Ala Ile Ser Val Leu His Glu Met Met Gln Gln Thr
        50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 12
<211> LENGTH: 166
<212> TYPE: PRT
<213> ORGANISM: Homo sapiens

<400> SEQUENCE: 12

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
                20                  25                  30

Arg His Asp Phe Gly Leu Pro Gln Glu Glu Phe Asp Gly Asn Gln Phe
            35                  40                  45

Gln Lys Thr Gln Ala Ile Ser Val Leu His Glu Met Ile Gln Gln Thr
        50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asn Leu
                85                  90                  95

Glu Ala Cys Val Ile Gln Glu Val Gly Met Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Ile Leu Arg Arg Lys Asp
                165
```

```
<210> SEQ ID NO 13
<211> LENGTH: 166
<212> TYPE: PRT
<213> ORGANISM: Homo sapiens

<400> SEQUENCE: 13

Cys Asp Leu Pro Gln Thr His Ser Leu Arg Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Glu Phe Arg Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Phe Ile Leu Ala Val Arg Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Phe Ser Phe Ser Thr Asn Leu Lys Lys
145                 150                 155                 160

Gly Leu Arg Arg Lys Asp
                165

<210> SEQ ID NO 14
<211> LENGTH: 166
<212> TYPE: PRT
<213> ORGANISM: Homo sapiens

<400> SEQUENCE: 14

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Ala Glu Ala Ile Ser Val Leu His Glu Val Ile Gln Gln Thr
    50                  55                  60

Phe Asn Leu Phe Ser Thr Lys Asp Ser Ser Val Ala Trp Asp Glu Arg
65                  70                  75                  80

Leu Leu Asp Lys Leu Tyr Thr Glu Leu Tyr Gln Gln Leu Asn Asp Leu
                85                  90                  95

Glu Ala Cys Val Met Gln Glu Val Trp Val Gly Gly Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Ser Ser Arg Asn Leu Gln Glu
145                 150                 155                 160
```

Arg Leu Arg Arg Lys Glu
            165

<210> SEQ ID NO 15
<211> LENGTH: 166
<212> TYPE: PRT
<213> ORGANISM: Homo sapiens

<400> SEQUENCE: 15

Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
            165

<210> SEQ ID NO 16
<211> LENGTH: 166
<212> TYPE: PRT
<213> ORGANISM: Homo sapiens

<400> SEQUENCE: 16

Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg Tyr Asp Phe Gly Phe Pro Gln Glu Val Phe Asp Gly Asn Gln Phe
        35                  40                  45

Gln Lys Ala Gln Ala Ile Ser Ala Phe His Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Ile Glu Leu Phe Gln Gln Leu Asn Asp Leu
                85                  90                  95

Glu Ala Cys Val Thr Gln Glu Val Gly Val Glu Glu Ile Ala Leu Met
            100                 105                 110

Asn Glu Asp Ser Ile Leu Ala Val Arg Lys Tyr Phe Gln Arg Ile Thr
        115                 120                 125

Leu Tyr Leu Met Gly Lys Lys Tyr Ser Pro Cys Ala Trp Glu Val Val
    130                 135                 140

```
Arg Ala Glu Ile Met Arg Ser Phe Ser Phe Ser Thr Asn Leu Gln Lys
145                 150                 155                 160

Gly Leu Arg Arg Lys Asp
                165

<210> SEQ ID NO 17
<211> LENGTH: 23
<212> TYPE: PRT
<213> ORGANISM: Artificial Sequence
<220> FEATURE:
<223> OTHER INFORMATION: signal sequence

<400> SEQUENCE: 17

Met Ala Leu Thr Phe Tyr Leu Leu Val Ala Leu Val Val Leu Ser Tyr
1               5                   10                  15

Lys Ser Phe Ser Ser Leu Gly
            20

<210> SEQ ID NO 18
<211> LENGTH: 23
<212> TYPE: PRT
<213> ORGANISM: Artificial Sequence
<220> FEATURE:
<223> OTHER INFORMATION: signal sequence

<400> SEQUENCE: 18

Met Ala Arg Ser Phe Ser Leu Leu Met Val Val Leu Val Leu Ser Tyr
1               5                   10                  15

Lys Ser Ile Cys Ser Leu Gly
            20

<210> SEQ ID NO 19
<211> LENGTH: 23
<212> TYPE: PRT
<213> ORGANISM: Artificial Sequence
<220> FEATURE:
<223> OTHER INFORMATION: signal sequence

<400> SEQUENCE: 19

Met Ala Leu Pro Phe Ala Leu Leu Met Ala Leu Val Val Leu Ser Cys
1               5                   10                  15

Lys Ser Ser Cys Ser Leu Asp
            20

<210> SEQ ID NO 20
<211> LENGTH: 23
<212> TYPE: PRT
<213> ORGANISM: Artificial Sequence
<220> FEATURE:
<223> OTHER INFORMATION: signal sequence

<400> SEQUENCE: 20

Met Ala Leu Ser Phe Ser Leu Leu Met Ala Val Leu Val Leu Ser Tyr
1               5                   10                  15

Lys Ser Ile Cys Ser Leu Gly
            20

<210> SEQ ID NO 21
<211> LENGTH: 23
<212> TYPE: PRT
<213> ORGANISM: Artificial Sequence
<220> FEATURE:
<223> OTHER INFORMATION: signal sequence

<400> SEQUENCE: 21
```

```
Met Ala Leu Thr Phe Ala Leu Leu Val Ala Leu Leu Val Leu Ser Cys
1               5                   10                  15

Lys Ser Ser Cys Ser Val Gly
            20
```

<210> SEQ ID NO 22
<211> LENGTH: 166
<212> TYPE: PRT
<213> ORGANISM: Homo sapiens

<400> SEQUENCE: 22

```
Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
    115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

<210> SEQ ID NO 23
<211> LENGTH: 121
<212> TYPE: PRT
<213> ORGANISM: Homo sapiens

<400> SEQUENCE: 23

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Trp Gly Ser Tyr Tyr Ala Ala Leu Asp Tyr Trp Gly
            100                 105                 110

Gln Gly Thr Leu Val Thr Val Ser Ser
    115                 120
```

<210> SEQ ID NO 24
<211> LENGTH: 113
<212> TYPE: PRT
<213> ORGANISM: Homo sapiens

<400> SEQUENCE: 24

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Phe Asp Val Pro Tyr Thr Phe Gly Gln Gly Thr Lys Val Glu Ile
            100                 105                 110

Lys
```

<210> SEQ ID NO 25
<211> LENGTH: 121
<212> TYPE: PRT
<213> ORGANISM: Homo sapiens

<400> SEQUENCE: 25

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Leu Glu Tyr Ala Phe Pro Asp Lys Phe Asp Tyr Trp Gly
            100                 105                 110

Gln Gly Thr Leu Val Thr Val Ser Ser
        115                 120
```

<210> SEQ ID NO 26
<211> LENGTH: 107
<212> TYPE: PRT
<213> ORGANISM: Homo sapiens

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
```

```
                35                  40                  45
Tyr Phe Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gln Gly Thr Lys Val Glu Ile Lys
            100                 105

<210> SEQ ID NO 27
<211> LENGTH: 123
<212> TYPE: PRT
<213> ORGANISM: Mus musculus

<400> SEQUENCE: 27

Glu Val Gln Leu Gln Gln Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
                 20                  25                  30

Gly Met Ser Trp Val Arg Gln Thr Pro Asp Lys Arg Leu Asp Trp Val
             35                  40                  45

Ser Ile Ile Thr Ser Gly Gly Ser Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Ala Glu Gly Gly Gly Asn Tyr Asp Tyr Ala Met Asp Tyr
            100                 105                 110

Trp Gly Gln Gly Thr Ser Val Thr Val Ser Ser
        115                 120

<210> SEQ ID NO 28
<211> LENGTH: 112
<212> TYPE: PRT
<213> ORGANISM: Mus musculus

<400> SEQUENCE: 28

Asp Ile Val Met Thr Gln Ala Ala Phe Ser Asn Pro Val Thr Leu Gly
 1               5                  10                  15

Thr Ser Ala Ser Ile Ser Cys Arg Ser Ser Lys Ser Leu Leu His Ser
                 20                  25                  30

Asn Gly Ile Thr Tyr Leu Tyr Trp Tyr Leu Gln Lys Pro Gly Gln Ser
             35                  40                  45

Pro Gln Leu Leu Ile Tyr Gln Met Ser Asn Leu Ala Ser Gly Val Pro
 50                  55                  60

Asp Arg Phe Ser Ser Ser Gly Ser Gly Ile Asp Phe Thr Leu Arg Ile
 65                  70                  75                  80

Ser Arg Val Glu Ala Glu Asp Val Gly Ala Tyr Tyr Cys Ala Gln Asn
                 85                  90                  95

Leu Glu Leu Pro Phe Thr Phe Gly Ser Gly Thr Lys Leu Glu Ile Lys
            100                 105                 110

<210> SEQ ID NO 29
<211> LENGTH: 119
<212> TYPE: PRT
```

-continued

<213> ORGANISM: Mus musculus

<400> SEQUENCE: 29

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Asn
            20                  25                  30

Asn Ile Asn Trp Val Lys Gln Arg Pro Gly Gln Gly Leu Glu Trp Ile
        35                  40                  45

Gly Trp Ile Tyr Pro Gly Ser Gly Asn Ile Lys Tyr Asn Glu Lys Phe
    50                  55                  60

Lys Gly Lys Ala Thr Leu Thr Val Asp Thr Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Ser Gly Trp Val Val Ala Trp Phe Pro Tyr Trp Gly Gln Gly
            100                 105                 110

Thr Thr Val Thr Val Ser Ser
            115

<210> SEQ ID NO 30
<211> LENGTH: 107
<212> TYPE: PRT
<213> ORGANISM: Mus musculus

<400> SEQUENCE: 30

Asp Ile Val Leu Thr Gln Ser Pro Val Ile Leu Ser Val Thr Pro Gly
1               5                   10                  15

Asp Ser Val Ser Leu Ser Cys Arg Ala Ser Gln Ser Ile Ser Asn His
            20                  25                  30

Leu His Trp Tyr Gln Gln Thr Ser His Glu Ser Pro Arg Leu Leu Ile
        35                  40                  45

Arg Phe Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Phe
                85                  90                  95

Thr Phe Gly Ser Gly Thr Lys Leu Glu Ile Lys
            100                 105

<210> SEQ ID NO 31
<211> LENGTH: 557
<212> TYPE: PRT
<213> ORGANISM: Homo sapiens

<400> SEQUENCE: 31

Met Met Val Val Leu Leu Gly Ala Thr Thr Leu Val Leu Val Ala Val
1               5                   10                  15

Ala Pro Trp Val Leu Ser Ala Ala Gly Gly Lys Asn Leu Lys Ser
            20                  25                  30

Pro Gln Lys Val Glu Val Asp Ile Ile Asp Asp Asn Phe Ile Leu Arg
        35                  40                  45

Trp Asn Arg Ser Asp Glu Ser Val Gly Asn Val Thr Phe Ser Phe Asp
    50                  55                  60

Tyr Gln Lys Thr Gly Met Asp Asn Trp Ile Lys Leu Ser Gly Cys Gln
65                  70                  75                  80

-continued

Asn Ile Thr Ser Thr Lys Cys Asn Phe Ser Ser Leu Lys Leu Asn Val
            85                  90                  95

Tyr Glu Glu Ile Lys Leu Arg Ile Arg Ala Glu Lys Glu Asn Thr Ser
        100                 105                 110

Ser Trp Tyr Glu Val Asp Ser Phe Thr Pro Phe Arg Lys Ala Gln Ile
    115                 120                 125

Gly Pro Pro Glu Val His Leu Glu Ala Glu Asp Lys Ala Ile Val Ile
130                 135                 140

His Ile Ser Pro Gly Thr Lys Asp Ser Val Met Trp Ala Leu Asp Gly
145                 150                 155                 160

Leu Ser Phe Thr Tyr Ser Leu Val Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

Ser Pro Glu Thr Thr Tyr Cys Leu Lys Val Lys Ala Ala Leu Leu Thr
        195                 200                 205

Ser Trp Lys Ile Gly Val Tyr Ser Pro Val His Cys Ile Lys Thr Thr
    210                 215                 220

Val Glu Asn Glu Leu Pro Pro Glu Asn Ile Glu Val Ser Val Gln
225                 230                 235                 240

Asn Gln Asn Tyr Val Leu Lys Trp Asp Tyr Thr Tyr Ala Asn Met Thr
                245                 250                 255

Phe Gln Val Gln Trp Leu His Ala Phe Leu Lys Arg Asn Pro Gly Asn
            260                 265                 270

His Leu Tyr Lys Trp Lys Gln Ile Pro Asp Cys Glu Asn Val Lys Thr
        275                 280                 285

Thr Gln Cys Val Phe Pro Gln Asn Val Phe Gln Lys Gly Ile Tyr Leu
    290                 295                 300

Leu Arg Val Gln Ala Ser Asp Gly Asn Asn Thr Ser Phe Trp Ser Glu
305                 310                 315                 320

Glu Ile Lys Phe Asp Thr Glu Ile Gln Ala Phe Leu Leu Pro Pro Val
                325                 330                 335

Phe Asn Ile Arg Ser Leu Ser Asp Ser Phe His Ile Tyr Ile Gly Ala
            340                 345                 350

Pro Lys Gln Ser Gly Asn Thr Pro Val Ile Gln Asp Tyr Pro Leu Ile
        355                 360                 365

Tyr Glu Ile Ile Phe Trp Glu Asn Thr Ser Asn Ala Glu Arg Lys Ile
    370                 375                 380

Ile Glu Lys Lys Thr Asp Val Thr Val Pro Asn Leu Lys Pro Leu Thr
385                 390                 395                 400

Val Tyr Cys Val Lys Ala Arg Ala His Thr Met Asp Glu Lys Leu Asn
                405                 410                 415

Lys Ser Ser Val Phe Ser Asp Ala Val Cys Glu Lys Thr Lys Pro Gly
            420                 425                 430

Asn Thr Ser Lys Ile Trp Leu Ile Val Gly Ile Cys Ile Ala Leu Phe
        435                 440                 445

Ala Leu Pro Phe Val Ile Tyr Ala Ala Lys Val Phe Leu Arg Cys Ile
    450                 455                 460

Asn Tyr Val Phe Phe Pro Ser Leu Lys Pro Ser Ser Ser Ile Asp Glu
465                 470                 475                 480

Tyr Phe Ser Glu Gln Pro Leu Lys Asn Leu Leu Leu Ser Thr Ser Glu
                485                 490                 495

```
Glu Gln Ile Glu Lys Cys Phe Ile Ile Glu Asn Ile Ser Thr Ile Ala
                500                 505                 510

Thr Val Glu Glu Thr Asn Gln Thr Asp Glu Asp His Lys Lys Tyr Ser
            515                 520                 525

Ser Gln Thr Ser Gln Asp Ser Gly Asn Tyr Ser Asn Glu Asp Glu Ser
        530                 535                 540

Glu Ser Lys Thr Ser Glu Glu Leu Gln Gln Asp Phe Val
545                 550                 555

<210> SEQ ID NO 32
<211> LENGTH: 331
<212> TYPE: PRT
<213> ORGANISM: Homo sapiens

<400> SEQUENCE: 32

Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
        195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Ser Ala Glu
225                 230                 235                 240

Ser Ala Lys Ile Gly Gly Ile Ile Thr Val Phe Leu Ile Ala Leu Val
                245                 250                 255

Leu Thr Ser Thr Ile Val Thr Leu Lys Trp Ile Gly Tyr Ile Cys Leu
            260                 265                 270

Arg Asn Ser Leu Pro Lys Val Leu Arg Gln Gly Leu Ala Lys Gly Trp
        275                 280                 285

Asn Ala Val Ala Ile His Arg Cys Ser His Asn Ala Leu Gln Ser Glu
    290                 295                 300

Thr Pro Glu Leu Lys Gln Ser Ser Cys Leu Ser Phe Pro Ser Ser Trp
305                 310                 315                 320
```

```
Asp Tyr Lys Arg Ala Ser Leu Cys Pro Ser Asp
            325                 330

<210> SEQ ID NO 33
<211> LENGTH: 4
<212> TYPE: PRT
<213> ORGANISM: Artificial Sequence
<220> FEATURE:
<223> OTHER INFORMATION: HCDR1 fragment of M43 antibody

<400> SEQUENCE: 33

Gly Gly Thr Phe
1

<210> SEQ ID NO 34
<211> LENGTH: 4
<212> TYPE: PRT
<213> ORGANISM: Artificial Sequence
<220> FEATURE:
<223> OTHER INFORMATION: Fragment of IFNalpha

<400> SEQUENCE: 34

Asp Arg His Asp
1

<210> SEQ ID NO 35
<211> LENGTH: 4
<212> TYPE: PRT
<213> ORGANISM: Artificial Sequence
<220> FEATURE:
<223> OTHER INFORMATION: Fragment of IFNomega

<400> SEQUENCE: 35

Asp Arg Arg Asp
1

<210> SEQ ID NO 36
<211> LENGTH: 5
<212> TYPE: PRT
<213> ORGANISM: Artificial Sequence
<220> FEATURE:
<223> OTHER INFORMATION: Fragment of IFNa
<220> FEATURE:
<221> NAME/KEY: VARIANT
<222> LOCATION: (3)..(3)
<223> OTHER INFORMATION: Xaa is any amino acid

<400> SEQUENCE: 36

Tyr Leu Xaa Glu Lys
1               5

<210> SEQ ID NO 37
<211> LENGTH: 5
<212> TYPE: PRT
<213> ORGANISM: Artificial Sequence
<220> FEATURE:
<223> OTHER INFORMATION: Fragment of IFNw

<400> SEQUENCE: 37

Tyr Leu Lys Glu Lys
1               5

<210> SEQ ID NO 38
<211> LENGTH: 8
<212> TYPE: PRT
<213> ORGANISM: Artificial Sequence
<220> FEATURE:
```

```
<223> OTHER INFORMATION: M88 LCDR1 fragment

<400> SEQUENCE: 38

Ser Gln Ser Ile Ser Ser Tyr Leu
1               5

<210> SEQ ID NO 39
<211> LENGTH: 14
<212> TYPE: PRT
<213> ORGANISM: Artificial Sequence
<220> FEATURE:
<223> OTHER INFORMATION: M43extendedLCDR1

<400> SEQUENCE: 39

Ser Gln Ser Val Leu Tyr Ser Ser Asn Asn Lys Asn Tyr Leu
1               5                   10

<210> SEQ ID NO 40
<211> LENGTH: 14
<212> TYPE: PRT
<213> ORGANISM: Artificial Sequence
<220> FEATURE:
<223> OTHER INFORMATION: LCDR1 library
<220> FEATURE:
<221> NAME/KEY: VARIANT
<222> LOCATION: (6)..(6)
<223> OTHER INFORMATION: X1 is any amino acid
<220> FEATURE:
<221> NAME/KEY: VARIANT
<222> LOCATION: (8)..(8)
<223> OTHER INFORMATION: X2 is any amino acid
<220> FEATURE:
<221> NAME/KEY: VARIANT
<222> LOCATION: (9)..(9)
<223> OTHER INFORMATION: X3 is any amino acid
<220> FEATURE:
<221> NAME/KEY: VARIANT
<222> LOCATION: (11)..(11)
<223> OTHER INFORMATION: X4 is any amino acid

<400> SEQUENCE: 40

Ser Gln Ser Val Leu Xaa Ser Xaa Xaa Asn Xaa Asn Tyr Leu
1               5                   10
```

INTERFERON ALPHA AND OMEGA ANTIBODY ANTAGONISTS

This application claims the benefit of U.S. Provisional Application No. 61/788,302, filed 15 Mar. 2013, the entire contents of which are incorporated herein by reference.

FIELD OF THE INVENTION

The present invention relates to broadly neutralizing interferon-α and interferon-ω antibody antagonists, polynucleotides encoding the antibodies or fragments, and methods of making and using the foregoing.

BACKGROUND OF THE INVENTION

Type I IFNs are a family of cytokines that all signal through an ubiquitously expressed heterodimeric receptor (IFNAR) resulting in antiviral, antiproliferative and immunomodulatory effects. In humans, type I IFN is composed of at least 12 IFNα protein subtypes and 1 subtype each for IFNβ, IFNϵ, IFNκ, and IFNω. Induction of type I IFN occurs in response to both sterile and microbial ligands. While the antiviral and antiproliferative effects of type I IFN have been exploited in the clinic for infectious disease and oncologic indications, antagonists of type I IFN are being developed for immune-mediated inflammatory indications.

Multiple immune-mediated inflammatory diseases, such as SLE, type I diabetes, psoriasis, primary Sjögren's disease, systemic sclerosis and rheumatoid arthritis, exhibit evidence of elevated type IFN to various degrees as determined by the overabundance of IFN-inducible gene transcripts commonly called the IFN-signature present in whole blood and/or tissue.

Type I IFN antagonist approaches currently in clinical development for lupus include multiple approaches to neutralize IFNα subtypes and not other type I IFNs (β, ϵ, κ, ω) using anti-IFNα antibodies, such as those described in U.S. Pat. No. 7,087,726, U.S. Pat. No. 8,025,882 and U.S. Pat. Appl. Publ. No. US2008/0160030. Clinical trial data indicates partial reduction of the type I IFN signature in patients treated with anti-IFNα antibodies (Merrill et al., Ann Rheum Dis 70:1905-1913, 2011; Yao et al., Arthritis Rheum 60:1785-1796, 2009) and improvement in signs and symptoms of SLE, flare rates, and steroid burden at week 24 in a pre-specified biomarker defined group of Interferon Signature Metric (ISM)-Low moderate to severely active lupus subjects. No efficacy was seen in patients pre-defined as ISM-High (Kalunian et al., 2012 ACR/ARHP Annual Meeting; Abstract #2622, 2012).

Anti-IFNAR1 antibodies are an alternative to treat lupus (Wang et al., 2013; Clinical Pharmacology & Therapeutics accepted article preview 14 Feb. 2013; doi: 10.1038/clpt.2013.35). IFNAR1 blockade would be predicted to abolish IFN signaling induced by all type I IFNs, including IFNβ. IFNβ may play a more critical role in antiviral defense, as specific deletion of the gene encoding IFNβ incurs substantial susceptibility to a host of viruses when compared to similarly exposed mice having functional IFNβ (Lazear et al., J Virol 85:7186-7194, 2011; Deonarain et al., J Virol 74: 3404-340, 2000; Deonarain et al., Circulation 110: 3540-3543, 2004; Gerlach, et al., J Virol 80: 3438-3444, 2006).

Therefore, there is a need for additional antibodies for the treatment of lupus and other immune-mediated inflammatory diseases.

BRIEF DESCRIPTION OF THE DRAWINGS

FIGS. 1A and 1B show inhibition of IP-10 release in whole blood induced by FIG. 1A) 100 U/ml endogenous leukocyte IFN (viral induced) or FIG. 1B) 250 U/ml recombinant human IFNω at specified concentrations.

FIG. 2 shows inhibition of Type I IFN induced by systemic lupus erythematosus (SLE) patient-derived immune complex by various antibodies as indicated. Combination of anti-IFNα1 and anti-IFNω, anti-IFNα2 and anti-IFNω or anti-IFNα3 and anti-IFNω provides more pronounced inhibition when compared to the anti-IFNα antibody alone. Broadly neutralizing anti-IFNα/IFNω antibody (M43) demonstrated further suppression of total activity.

FIG. 3 shows percent (%) inhibition of elevated SLE gene signature with anti-IFNω, anti-IFNα antibody or a combination of the two. Baseline elevated IFN-inducible gene expression in the absence of antibody treatment is normalized to 100%.

FIG. 4 shows the overall molecular structure of IFNω/FabM43 complex. Labeled H is VH; labeled L is VL, and top left is IFNω.

FIG. 5 shows the overall molecular structures of FIG. 5A) IFNα4A/Fab357 and FIG. 5B) IFNω/Fab357 complexes. Only the Fv part is shown for the Fab. Fab537 is Fab of C2595.

FIG. 6 A) shows the overall molecular structure of IFNα4A/FabM88 complex. FIG. 6B) Representative electron density (2mFo-DFc at 1.5σ) around the part of epitope region in the antigen combining site. Labeled H is VH; labeled L is VL; top left is IFNα4A.

FIG. 7 shows the IFNα4A structure and comparison with IFNω and IFNα. FIG. 7A) IFNα4A. The five main helices are labeled. The long connecting loop AB is also labeled next to the short helical segment. FIG. 7B) IFNω (pdb code 3se4) and FIG. 7C) IFNβ (pdb id 1au1). FIG. 7D) Structural comparison with IFNβ. The main differences around the AB helical segment are indicated by an oval.

FIG. 8. Mode of neutralization by M88. The IFNω/IFNAR1/IFNAR2 structure (pdb id 3se4) and M88/IFNα4 are overlaid on the IFNs.

SUMMARY OF THE INVENTION

One aspect of the invention is an isolated monoclonal antibody that binds to and neutralizes activity of human interferon omega (IFNω) and at least four, five, six, seven, eight, nine or ten human interferon alpha (IFNα) subtypes.

In other aspects of the invention, the isolated antibody competes for binding to the human IFNω and the human IFNα subtypes IFNαB2, IFNαF, IFNαG and/or IFNαJ1 with an isolated antibody comprising:

- a heavy chain variable region (VH) amino acid sequence of SEQ ID NO: 23 and a light chain variable region (VL) amino acid sequence of SEQ ID NO: 24; or
- a VH amino acid sequence of SEQ ID NO: 27 and a VL amino acid sequence of SEQ ID NO: 28.

In further aspects of the invention, the isolated antibody binds IFNω at one or more residues F27, L30 and R33 of SEQ ID NO: 1; the isolated antibody binds IFNα4a at one or more residues F27, L30 and R33 of SEQ ID NO: 19; the isolated antibody inhibits activity of systemic lupus erythematosus (SLE) immune complex-induced IFN.

Additional aspects of the invention are an isolated polynucleotide encoding an antibody of the invention; and a pharmaceutical composition comprising the antibody of the invention and a pharmaceutically accepted carrier.

A further aspect of the invention is a method of treating or preventing a disease associated with increased production of IFNα and IFNω, comprising administering a therapeutically effective amount of an isolated antibody of the invention to a patient in need thereof for a time sufficient to treat or prevent the disease. In an additional aspect of the invention, the disease associated with increased production of IFNα and IFNω is systemic lupus erythematosus (SLE).

Another aspect of the invention is a method of inhibiting interaction of IFNω and IFNα subtypes IFNαB2, IFNαF, IFNαG and/or IFNαJ1 with IFNAR in a patient need thereof, comprising administering an isolated antibody of the invention to a patient for a time sufficient to prevent the interaction of IFNω and IFNα subtypes IFNαB2, IFNαC, IFNαF, IFNαG and/or IFNαJ1 with IFNAR.

DETAILED DESCRIPTION OF THE INVENTION

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein can be used in the practice for testing of the present invention, exemplary materials and methods are described herein. In describing and claiming the present invention, the following terminology will be used.

The term "specific binding" or "specifically binds" or "binds" as used herein refers to antibody binding to a predetermined antigen with greater affinity than for other antigens. Typically, the antibody binds to a predetermined antigen with a dissociation constant ($K_D$) of $1\times10^{-7}$ M or less, for example $1\times10^{-8}$ M or less, $1\times10^{-9}$ M or less, $1\times10^{-10}$ M or less, $1\times10^{11}$ M or less, or $1\times10^{-12}$ M or less, typically with a $K_D$ that is at least ten fold less than its $K_D$ for binding to a non-specific antigen or epitope (e.g., BSA, casein). The dissociation constant can be measured using standard procedures. Antibodies that specifically bind to a predetermined antigen may, however, have cross-reactivity to other related antigens, for example to the same predetermined antigen from other species (homologs), such as human or monkey, for example *Macaca fascicularis* (cynomolgus, cyno) or *Pan troglodytes* (chimpanzee, chimp) Antibodies that specifically bind to a predetermined antigen can further bind an epitope that is shared between two or more distinct antigens such as interferon alpha (IFNα) and interferon omega (IFNω); i.e. antibodies cross-react with IFNα and IFNω.

The term "neutralizing" or "neutralizes" or "neutralizing antibody" or "antibody antagonist" as used herein refers to an antibody or antibody fragment that partially or completely inhibits, by any mechanism, interferon alpha (IFNα) and/or interferon omega (IFNω) biological activity. Neutralizing antibodies can be identified using assays for IFNα and/or IFNω biological activity as described below. IFNα and/or IFNω neturalizing antibody may inhibit measured IFNα and IFNω biological activity by 20%, 30%, 40%, 50%, 60%, 70%, 75%, 80%, 85%, 90%, 95%, 96%, 97%, 98%, 99% or 100%.

The term "interferon-α" (IFNα) as used herein refers to all native subtypes of human alpha interferons. Native IFNα consists of more than 23 closely related protein subtypes encoded by distinct genes with a high degree of structural homology (Weissmann and Weber, Prog. Nucl. Acid. Res. Mol. Biol., 33: 251, 1986; Roberts et al., J. Interferon Cytokine Res. 18: 805-816, 1998). The human IFNα subtypes are at least IFNαA (IFNα2) (SEQ ID NO: 5), IFNαB2 (IFNα8) (SEQ ID NO: 6), IFNαC (IFNα10) (SEQ ID NO: 7), IFNαD (IFNα1) (SEQ ID NO: 8), IFNαF (IFNα21) (SEQ ID NO: 9), IFNαG (IFNα5) (SEQ ID NO: 10), and IFNαH (IFNα14) (SEQ ID NO: 11), IFNαI with P34H substitution (IFNα 17) (SEQ ID NO: 12), IFNαJ1 (IFNα7) (SEQ ID NO: 14), IFNαK (IFNα6) (SEQ ID NO: 14), IFNα4b (IFNα4) (SEQ ID NO: 15), and IFNαWA (IFNα6) (SEQ ID NO: 16). Nomenclature for human interferons is found at: http://www_genenames_org/genefamilies/_IFN.

The term IFNω as used herein refers to human IFNω having the amino acid sequence shown in SEQ ID NO: 1 and UniProt accession number P05000.

The term "type I interferon" refers to all native subtypes of human interferon-α and one subtype of interferon-β, interferon-ε, interferon-ω and interferon-κ which bind to a common interferon receptor IFNAR.

As used herein the term "IFNAR" refers to the well known interferon receptor which is a heterodimer or IFNAR1 and IFNAR2. IFNAR1 and IFNAR2 protein sequences are shown in SEQ ID NOs: 31 and 32, respectively. IFNAR1 mature extracellular domain spans residues 28-436 of SEQ ID NO: 31 and IFNAR2 mature extracellular domain spans residues 27-243 of SEQ ID NO: 32.

The term "antibodies" as used herein is meant in a broad sense and includes immunoglobulin molecules including polyclonal antibodies, monoclonal antibodies including murine, human, human-adapted, humanized and chimeric monoclonal antibodies, antibody fragments, bispecific or multispecific antibodies formed from at least two intact antibodies or antibody fragments, dimeric, tetrameric or multimeric antibodies, and single chain antibodies.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (λ), based on the amino acid sequences of their constant domains.

The term "antibody fragments" refers to a portion of an immunoglobulin molecule that retains the heavy chain and/or the light chain antigen binding site, such as a heavy chain complementarity determining regions (HCDR) 1, 2 and 3, a light chain complementarity determining regions (LCDR) 1, 2 and 3, a heavy chain variable region (VH), or a light chain variable region (VL). Antibody fragments include well known Fab, F(ab')2, Fd and Fv fragments as well as a domain antibodies (dAb) consisting one VH domain. VH and VL domains can be linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO 1992/01047.

An antibody variable region consists of a "framework" region interrupted by three "antigen binding sites". The antigen binding sites are defined using various terms: (i) Complementarity Determining Regions (CDRs), three in the VH (HCDR1, HCDR2, HCDR3), and three in the VL (LCDR1, LCDR2, LCDR3), are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3), refer to the regions of an antibody variable domains which are hypervariable in structure as defined by Chothia and Lesk (Chothia and Lesk, Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Chothia residues" as used herein are the antibody VL and VH residues numbered according to Al-Lazikani (Al-Lazikani et al., J Mol Biol 273:927-48, 1997).

"Framework" or "framework sequences" are the remaining sequences of a variable region other than those defined to be antigen binding site. Because the antigen binding site can be defined by various terms as described above, the exact amino acid sequence of a framework depends on how the antigen-binding site was defined.

"Human antibody" or "fully human antibody" refers to an antibody containing variable region and constant region sequences derived from human immunoglobulin sequences. Human antibodies of the invention may include substitutions so that they may not be exact copies of expressed human immunoglobulin or germline gene sequences. However, antibodies in which antigen binding sites are derived from a non-human species are not included in the definition of "human antibody".

"Human-adapted" antibodies or "human framework adapted (HFA)" antibodies refers to antibodies adapted according to methods described in U.S. Pat. Publ. No. US2009/0118127 and also refers to antibodies in which antigen-binding site sequences derived from non-human species are grafted onto human frameworks.

"Humanized antibodies" refers to antibodies in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

The term "monoclonal antibody" as used herein refers to a preparation of antibody molecules of single molecular composition. A monoclonal antibody composition displays a single binding specificity and affinity for a particular epitope.

The term "substantially identical" as used herein means that the two antibody variable region amino acid sequences being compared are identical or have "insubstantial differences". Insubstantial differences are substitutions of 1, 2, 3, 4, 5, 6, 7, 8, 9, 10, or 11 amino acids in an antibody or antibody variable region sequence that do not adversely affect antibody properties Amino acid sequences substantially identical to the variable region sequences disclosed herein are within the scope of the application. In some embodiments, the sequence identity can be about 90%, 91%, 92%, 93%, 94%, 95%, 96%, 97%, 98%, 99% or higher. Percent identity can be determined for example by pairwise alignment using the default settings of the AlignX module of Vector NTI v.9.0.0 (Invitrogen, Carslbad, Calif.). The protein sequences of the present invention can be used as a query sequence to perform a search against public or patent databases to, for example, identify related sequences. Exemplary programs used to perform such searches are the XBLAST or BLASTP programs (http//www_ncbi_nlm/nih_gov), or the GenomeQuest™ (GenomeQuest, Westborough, Mass.) suite using the default settings.

The term "epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

The term "paratope" as used herein means a portion of an antibody to which an antigen specifically binds. A paratope can be linear in nature or can be discontinuous, formed by a spatial relationship between non-contiguous amino acids of an antibody rather than a linear series of amino acids. A "light chain paratope" and a "heavy chain paratope" or "light chain paratope amino acid residues" and "heavy chain paratope amino acid residues" refer to antibody light chain and heavy chain residues in contact with an antigen, respectively.

"Bispecific" as used herein refers to an antibody that binds two distinct antigens or two discinct epitopes within an antigen. The bispecific antibodies may bind two or more distinct antigens in those cases where the bispecific antibodies cross-react with IFNα and IFNω.

"Monospecific" as used herein refers to an antibody that binds one antigen or one epitope. The monospecific antibodies may bind two or more distinct antigens in those cases where the monospecific antibodies cross-react with IFNα and IFNω.

The term "in combination with" as used herein means that the described agents can be administered to an animal together in a mixture, concurrently as single agents or sequentially as single agents in any order.

The term "IFNα biological activity" and "IFNω biological activity" as used herein refers to any activity occurring as a result of IFNα and IFNω, respectively, binding to its receptor IFNAR. One IFNα and IFNω biological activity is the ability of IFNα and IFNω to induce secreted embryonic alkaline phosphatase (SEAP) expression under the interferon inducible promoter such as ISG54 in HEK293 cells stably expressing signal transducer and activator of transcription 2 (STAT2), interferon regulatory factor 9 (IRF9) and SEAP using standard methods. Another IFNα and IFNω biological activity is the induction of chemokine IP-10 (CXCL10) production from peripheral blood mononuclear cells (PBMCs) or whole blood as described herein.

TABLE 1

| Amino acid | Three-letter code | One-letter code |
| --- | --- | --- |
| Alanine | ala | A |
| Arginine | arg | R |
| Asparagine | asn | N |
| Aspartate | asp | D |
| Cysteine | cys | C |
| Glutamate | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "polypeptide" or "protein" means a molecule that comprises at least two amino acid residues linked by a peptide bond to form a polypeptide. Small polypeptides of less than 50 amino acids may be referred to as "peptides".

Conventional one and three-letter amino acid codes are used herein as shown in Table 1.

Compositions of Matter

The present invention provides monoclonal antibodies that bind to and neutralize activity of human interferon omega (IFNω) and multiple human interferon alpha (IFNα) subtypes (IFNα/ω antibodies). The invention is based, at least in part, on the identification of a minimal neutralizing epitope shared by IFNω and multiple IFNα subtypes to which the IFNα/ω antibodies of the invention bind. The IFNα/ω antibodies of the invention are more potent in neutralizing SLE-relevant preparations of type I IFN and IFN signatures than antibodies neutralizing IFNα subtypes but not IFNω, and may therefore be more efficacious in treating any disease that is associated with increased production of IFNα and IFNω, such as immune-mediated inflammatory diseases. As the IFNα/ω antibodies of the invention do not neutralize IFNβ, they may have more favorable safety and PK profiles when compared to the anti-IFNAR therapies, which are expected to block all type I IFNs. "IFNα/ω antibodies" as used herein refers to antibodies that bind to and neutralize INFω and multiple IFNα subtypes as exemplified herein.

One embodiment of the invention is a monoclonal antibody that binds to and neutralizes activity of human interferon omega (IFNω) and at least four, five, six, seven, eight, nine or ten human interferon alpha (IFNα) subtypes.

The antibodies of the invention may neutralize IFNα subtypes IFNαB2, IFNαF, IFNαG and IFNαJ1. The antibodies of the invention may neutralize IFNα subtypes IFNαB2, IFNαC, IFNαF, IFNαG and IFNαJ1. The antibodies of the invention may neutralize IFNα subtypes IFNαB2, IFNαC, IFNαF, IFNαG, IFNαJ1 and IFNαA. The antibodies of the invention may neutralize IFNα subtypes IFNαB2, IFNαC, IFNαF, IFNαG, IFNαJ1, IFNαA and IFNαH2. The antibodies of the invention may neutralize IFNα subtypes IFNαB2, IFNαC, IFNαF, IFNαG, IFNαJ1, IFNαA, IFNαH2 and IFNαK. The antibodies of the invention may neutralize IFNα subtypes IFNαB2, IFNαC, IFNαF, IFNαG, IFNαJ1, IFNαA, IFNαH2, IFNαK and IFNαWA. The antibodies of the invention may neutralize IFNα subtypes IFNαB2, IFNαC, IFNαF, IFNαG, IFNαJ1, IFNαA IFNαH2, IFNαK, IFNαWA and IFNα4a.

The antibodies of the invention can be tested for their ability to neutralize IFNα and IFNω in a reporter gene assay using cell lines expressing reporter genes under an interferon responsive promoter, and stimulating cells with various IFNα subtypes and/or IFNω. For example, HEK-Blue™ IFN-α/β cells (InvivoGen, San Diego, Calif.) engineered to express a fully active type I IFN signaling pathway (stably expressing STAT2 and IRF9) and transfected with a SEAP reporter gene under the control of the IFNα/β inducible ISG54 promoter can be used as described herein. Signal from the alkaline phosphatase can be detected using well known reagents and the signal can be read on a spectrophotometer, and an $IC_{50}$ can be calculated for the inhibition using standard methods.

In one embodiment, the antibodies of the invention inhibit the activity of the human IFNω with an $IC_{50}$ value of about $5\times10^{-8}$ M or less, about $1\times10^{-8}$ M or less, about $1\times10^{-9}$ M or less, about $1\times10^{-10}$ M or less, about $1\times10^{-11}$ M or less or about $1\times10^{-12}$ M or less, and inhibits the activity of the human IFNα subtypes IFNαB2, IFNαF, IFNαG or IFNαJ1 with an $IC_{50}$ value of about $5\times10^{-8}$ M or less, about $1\times10^{-8}$ M or less, about $1\times10^{-9}$ M or less, about $1\times10^{-10}$ M or less, about $1\times10^{-11}$ M or less or about $1\times10^{-12}$ M or less, when the activity of the human IFNω and the human IFNα subtypes is inhibition of secreted embryonic alkaline phosphatase (SEAP) expression under the interferon inducible ISG54 promoter in HEK293 cells stably expressing signal transducer and activator of transcription 2 (STAT2), interferon regulatory factor 9 (IRF9) and SEAP. The antibodies of the invention "neturalize" IFNω and/or any IFNα subtype when the $IC_{50}$ value is about $5\times10^{-8}$ or less, for example about $1\times10^{-8}$ M or less, about $1\times10^{-9}$ M or less, about $1\times10^{-10}$ M or less, about $1\times10^{-11}$ M or less, or about $1\times10^{-12}$ M or less in the assay "ISRE reporter gene assay" as described herein in Example 3.

Antibodies of the invention can also be tested for their IFNα and IFNω neutralizing ability by assessing their ability to inhibit IFN-induced cytokine release, such as IP-10 release from IFN-induced peripheral blood mononuclear cells (PBMCs) or whole blood. For example, PBMCs are isolated from heparinized whole blood from healthy volunteers using standard protocols, treated with a preformed complex of IFN and antibody to be tested, and IP-10 release is measured using standard methods such as Milliplex cytokine/chemokine kit (Millipore, Premixed 39 plex). Antibodies that neutralize IFNα and IFNω may inhibit IP-10 release by at least 30%, 40%, 50%, 60%, 70%, 75%, 80%, 85%, 90%, 95%, 96%, 97%, 98%, 99% or 100% when compared to IFN-induced IP-10 release in the absence of the antibody.

Antibodies of the invention may bind and neutralize least four, five, six, seven, eight, nine or ten IFNα subtypes in addition to neutralizing IFNω. The IFNα subtypes and IFNω may be produced by recombinant expression using standard methods. Exemplary signal sequences that can be used for directing secretion are shown in SEQ ID NOs: 17-21.

The antibodies of the invention bind human IFNω with a dissociation constant ($K_D$) of about $5\times10^{-9}$ M or less, about $1\times10^{-9}$ M or less, about $5\times10^{-10}$ M or less, about $1\times10^{-10}$ M or less, about $5\times10^{-11}$ M or less, about $1\times10^{-11}$ M or less, about $5\times10^{-12}$ M or less or about $1\times10^{-12}$ M or less, and bind the human IFNα subtypes IFNαB2, IFNαF, IFNαG or IFNαJ1 with a $K_D$ of about $5\times10^{-9}$ M or less, about $1\times10^{-9}$ M or less, about $5\times10^{-10}$ M or less, about $1\times10^{-10}$ M or less, about $5\times10^{-11}$ M or less, about $1\times10^{-11}$ M or less, about $5\times10^{-12}$ M or less, or about $1\times10^{-12}$ M or less.

The affinity of an antibody to IFNω or IFNα subtypes can be determined experimentally using any suitable method. Such methods may utilize ProteOn™ XPR36 (protein interaction array system) XPR36, Biacore 3000 or KinExA instrumentation, ELISA or competitive binding assays known to those skilled in the art. The measured affinity of a particular antibody/IFNω or IFNα subtypes interaction can vary if measured under different conditions (e.g., osmolarity, pH). Thus, measurements of affinity and other binding parameters (e.g., $K_D$, $K_{on}$, $K_{off}$) are preferably made with standardized conditions and a standardized buffer, such as the buffer described herein. Skilled in the art will appreciate that the internal error for affinity measurements for example using Biacore 3000 or ProteOn™ XPR36 (protein interaction array system) (measured as standard deviation, SD) can typically be within 5-33% for measurements within the typical limits of detection. Therefore the term "about" reflects the typical standard deviation in the assay. For example, the typical SD for a $K_D$ of $1\times10^{-9}$M is up to $\pm0.33\times10^{-9}$M.

The antibodies binding human IFNω and IFNα subtypes with a desired affinity and neutralization profile can be selected from libraries of variants or fragments by panning with human IFNω and IFNα subtypes and optionally by further antibody affinity maturation. In an exemplary panning campaign, phage libraries can be panned sequentially or using a mixture of chimpanzee IFNω, and human IFNα subtypes IFNα2, IFNα1, IFNαH2, IFNαG and IFNαF. Alternatively, antibodies of the invention can be made by immunizing mice with chimpanzee and cynomolgus IFNω, human IFNα subtypes IFNαD, IFNαJ1, IFNαC, IFNαB2, IFNαH2, IFNαA, IFNα4a, IFNαG, IFNαF, IFNαWA and IFNαI, and screening the hybridomas using standard methods.

Antibodies can be identified based on their inhibition of IFNω and IFNα biological activity using any suitable method and methods described herein.

One embodiment of the invention is an isolated monoclonal antibody that binds to and neutralizes activity of human interferon omega (IFNω) and at least four, five, six, seven, eight, nine or ten human interferon alpha (IFNα) subtypes, wherein the antibody competes for binding to the human IFNω and the human IFNα subtypes IFNαB2, IFNαF, IFNαG or IFNαJ1 with an isolated antibody comprising:

- a heavy chain variable region (VH) amino acid sequence of SEQ ID NO: 23 and a light chain variable region (VL) amino acid sequence of SEQ ID NO: 24; or
- a VH amino acid sequence of SEQ ID NO: 27 and a VL amino acid sequence of SEQ ID NO: 28.

Competition between specific binding to human IFNω and the human IFNα subtypes IFNαB2, IFNαF, IFNαG and/or IFNαJ1 with antibodies of the invention comprising certain VH and VL sequences can be assayed in vitro using well known methods. For example, binding of MSD Sulfo-Tag™ NHS-ester-labeled antibody to human to human IFNω and the human IFNα subtypes IFNαB2, IFNαF, IFNαG or IFNαJ1 in the presence of an unlabeled antibody can be assessed by ELISA, or Bioacore analyses or flow cytometry may be used to demonstrate competition with the antibodies of the current invention. Alternatively, real-time label-free competitive binding assays using Octet (ForteBio, Menlo Park, Calif.) can be used as described herein. The ability of a test antibody to inhibit the binding of the antibody comprising the VH of SEQ ID NO: 23 and the VL of SEQ ID NO: 24 or the VH of SEQ ID NO: 27 and the VL of SEQ ID NO: 28 to human IFNω and the human IFNα subtypes IFNαB2, IFNαF, IFNαG and/or IFNαJ1 demonstrates that the test antibody competes with these antibodies for binding to human IFNω and the human IFNα subtypes IFNαB2, IFNαF, IFNαG and/or IFNαJ1.

In another embodiment, the antibody of the invention binds IFNω at one or more residues F27, L30 and R33 of SEQ ID NO: 1.

In another embodiment, the antibody of the invention binds IFNα4a at one or more residues F27, L30 and R33 of SEQ ID NO: 19.

The residues F27, L30 and R33 in both IFNω and IFNα4a define a minimal epitope required for broad neutralizing activity of the IFNα/ω antibodies of the invention. Crystal structure of several antibody/IFNα or antibody/IFNω complexes revealed the three residues provide predominant contributions to antibody binding Human IFNα4a shares at least 83% identify with other human IFNαs and 59% identity with human IFNω. The F27 residue is conserved in all human IFNαs except IFNαD (al). F27 is also conserved in human IFNω. Both L30 and R33 are conserved in all human IFNαs as well as in human IFNω.

In another embodiment of the invention, the monoclonal antibody of the invention that binds to and neutralizes activity of human interferon omega (IFNω) and at least four, five, six, seven, eight, nine or ten human interferon alpha (IFNα) subtypes does not bind and does not neutralize IFNαD.

Antibodies of the invention binding specific IFNω and IFNα residues can be made by immunizing mice expressing human immunoglobulin loci (Lonberg et al., Nature 368: 856-9, 1994; Fishwild et al., Nature Biotechnology 14:845-51, 1996; Mendez et al., Nature Genetics 15:146-56, 1997, U.S. Pat. Nos. 5,770,429, 7,041,870, and 5,939,598) or Balb/c mice with the peptides comprising the epitope contact residues, for example a peptide having an amino acid sequence of an AB loop of IFNω (amino acid residues 22-34 of FNω of SEQ ID NO:1) or an AB loop of IFNα4a (amino acid residues 22-34 of IFNα4a of SEQ ID NO: 19), or a mixture of IFNω and IFNα subtypes as described herein and using the hybridoma method of Kohler et al., Nature 256: 495-97, 1975. The resulting antibodies are tested for their ability to compete with antibodies of the present invention, such as antibodies having the VH of SEQ ID NO: 23 and the VL of SEQ ID NO: 24 and tested for their binding to the epitope using standard methods. For example, when the structures of both individual components are known, in silico protein-protein docking can be carried out to identify compatible sites of interaction. Hydrogen-deuterium (H/D) exchange can be carried out with the antigen and antibody complex to map regions on the antigen that may be bound by the antibody. Segment and point mutagenesis of the antigen can be used to locate amino acids important for antibody binding. Co-crystal structure of antibody-antigen complex can be used to identify residues contributing to the epitope and paratope. The identified mAbs can further be modified by incorporating altered framework support residues to preserve binding affinity by techniques such as those disclosed in Queen et al., Proc Natl Acad Sci (USA) 86:10029-32, 1989 and Hodgson et al., Bio/Technology 9:421, 1991.

In another embodiment, the antibody of the invention binds IFNω at one or more residues F27, L30 and R33, and further binds at least one IFNω residue selected from the group consisting of residues P26, K31 and R34 of SEQ ID NO: 1.

In another embodiment, the antibody of the invention binds IFNω at one or more residues F27, L30 and R33, and further binds at least one IFNω residue selected from the group consisting of residues R22, R23, I24, S25, P26, K31, D32, R34, D35, Q40, K134, M146, E147, M149, K150, F153 and L154 of SEQ ID NO: 1.

In another embodiment, the antibody of the invention binds IFNω of SEQ ID NO: 1 at one or more residues R22, P26, F27, L30, K31, D32, R33, R34, D35, Q40, K134, M146, E147, M149, K150, F153 and L154.

In another embodiment, the antibody of the invention binds IFNω of SEQ ID NO: 1 at one or more residues R23, I24, S25, P26, F27, L30, K31, R33, R34, M146, E147, M149 and K150.

In another embodiment, the antibody of the invention binds IFNα4a at one or more residues F27, L30 and R33, and further binds at least one IFNα4a residue selected from the group consisting of residues H26, K31 and R34 of SEQ ID NO: 19.

In another embodiment, the antibody of the invention binds IFNα4a at one or more residues F27, L30 and R33, and further binds at least one IFNα4a residue selected from the group consisting of A19, H26, F27, L30, K31, D32, R33, H34, D35, V143, A146, E147, M149, R150 and S153 of SEQ ID NO: 19.

In another embodiment, the antibody of the invention binds IFNα4a of SEQ ID NO: 19 at one or more residues A19, H26, F27, L30, K31, D32, R33, H34, D35, V143, A146, E147, M149, R150 and S153 of SEQ ID NO: 19.

In another embodiment, the antibody of the invention binds IFNα4a of SEQ ID NO: 19 at one or more residues G22, R23, I24, S25, H26, F27, C29, L30, K31, R33, H34 V143, A146, E147 and R150 and S153 of SEQ ID NO: 19.

In other embodiments, the antibodies of the invention inhibit activity of viral-induced leukocyte interferon.

In some embodiments, the activity of viral-induced leukocyte interferon is IP-10 release in whole blood induced by 100 U/ml of interferon.

Antibodies of the invention may neutralize interferon produced by activated leukocytes, as assessed by their ability to inhibit IP-10 release in whole blood induced by 100 U/ml interferon as described herein. Antibodies of the invention may neutralize effects of interferon produced by activated leukocytes by at least 30%, 40%, 50%, 60%, 70%, 75%, 80%, 85%, 90%, 95%, 96%, 97%, 98%, 99% or 100% in the presence of 50 μg/ml antibody.

In some embodiments, the antibodies of the invention inhibit IP-10 release in whole blood by more than 50% in the presence of 50 μg/ml antibody.

In another embodiment, the antibodies or the invention inhibit SLE immune complex-induced IFN production. SLE immune complex represent the type I IFN milieu present tin SLE. The IFN production can be measured using the reporter gene assay as described herein.

In some embodiments, antibodies of the invention may inhibit SLE immune complex-induced interferon production by at least 30%, 40%, 50%, 60%, 70%, 75%, 80%, 85%, 90%, 95%, 96%, 97%, 98%, 99% or 100%.

The antibodies of the invention may be human, humanized or human-adapted

The antibodies of the invention may be of IgA, IgD, IgE, IgG or IgM type. The antibodies of the invention may be of IgG1, IgG2, IgG3, IgG4 type.

Another embodiment of the invention is an isolated antibody comprising:

- a heavy chain variable region (VH) amino acid sequence of SEQ ID NO: 23 and a light chain variable region (VL) amino acid sequence of SEQ ID NO: 24;
- a VH amino acid sequence of SEQ ID NO: 25 and a VL amino acid sequence of SEQ ID NO: 26; or
- a VH amino acid sequence of SEQ ID NO: 27 and a VL amino acid sequence of SEQ ID NO: 28.

Human mAbs lacking any non-human sequences can be prepared and optimized from phage display libraries by techniques referenced in, e.g., Knappik et al., J Mol Biol 296:57-86, 2000; and Krebs et al., J Immunol Meth 254: 67-84 2001. In an exemplary method, the antibodies of the invention are isolated from libraries expressing antibody heavy and light chain variable regions as fusion proteins with bacteriophage pIX coat protein. The antibody libraries are screened for binding to human IFNω and IFNα and the obtained positive clones are further characterized, the Fabs isolated from the clone lysates, and expressed as full length IgGs. Exemplary antibody libraries and screening methods are described in Shi et al., J Mol Biol 397:385-96, 2010; Int. Pat. Publ. No. WO2009/085462, and U.S. Ser. No. 12/546,850; U.S. Pat. Nos. 5,223,409, 5,969,108, and 5,885,793).

The resulting mAbs can further be modified in their framework regions to change certain framework residues to those present in a matching human germline.

Immune effector properties of the antibodies of the invention may be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), phagocytosis, down regulation of cell surface receptors (e.g., B cell receptor; BCR), etc. can be provided and/or controlled by modifying residues in the Fc responsible for these activities. Pharmacokinetic properties could also be enhanced by mutating residues in the Fc domain that extend antibody half-life (Strohl Curr Opin Biotechnol 20:685-91, 2009).

Additionally, antibodies of the invention can be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function (Knigh et al., Platelets 15:409-18, 2004; Leong et al., Cytokine 16:106-19, 2001; Yang et al., Protein Eng 16:761-70, 2003).

Antibodies or fragments thereof of the invention modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al., J Mol Biol 305:989-1010, 2001). Potential structure destabilizing residues may be identified based upon the crystal structure of the antibody or by molecular modeling in certain cases, and the effect of the residues on antibody stability can be tested by generating and evaluating variants harboring mutations in the identified residues. One of the ways to increase antibody stability is to raise the thermal transition midpoint (Tm) as measured by differential scanning calorimetry (DSC). In general, the protein Tm is correlated with its stability and inversely correlated with its susceptibility to unfolding and denaturation in solution and the degradation processes that depend on the tendency of the protein to unfold (Remmele et al., Biopharm 13:36-46, 2000). A number of studies have found correlation between the ranking of the physical stability of formulations measured as thermal stability by DSC and physical stability measured by other methods (Gupta et al., AAPS PharmSci 5E8, 2003; Zhang et al., J Pharm Sci 93:3076-89, 2004; Maa et al., Int J Pharm 140:155-68, 1996; Bedu-Addo et al., Pharm Res 21:1353-61, 2004; Remmele et al., Pharm Res 15:200-8, 1997). Formulation studies suggest that a Fab Tm has implication for long-term physical stability of a corresponding mAb. Differences in amino acids in either framework or within the CDRs could have significant effects on the thermal stability of the Fab domain (Yasui et al., FEBS Left 353:143-6, 1994).

IFNα/ω antibodies of the invention can be engineered into bispecific antibodies which are also encompassed within the scope of the invention. The VL and/or the VH regions of the antibodies of the invention can be engineered using published methods into single chain bispecific antibodies as structures such as TandAb® designs (Int. Pat. Publ. No. WO1999/57150; U.S. Pat. Publ. No. US2011/0206672) or into bispecific scFVs as structures such as those disclosed in U.S. Pat. No. 5,869,620; Int. Pat. Publ. No. WO1995/15388A, Int. Pat. Publ. No. WO1997/14719 or Int. Pat. Publ. No WO2011/036460.

The VL and/or the VH regions of the antibodies of the invention can be engineered into bispecific full length antibodies, where each antibody arm binds a distinct antigen or epitope. Such bispecific antibodies are typically made by modulating the CH3 interactions between the two antibody heavy chains to form bispecific antibodies using technologies such as those described in U.S. Pat. No. 7,695,936; Int. Pat. Publ. No. WO04/111233; U.S. Pat. Publ. No. US2010/0015133; U.S. Pat. Publ. No. US2007/0287170; Int. Pat. Publ. No. WO2008/119353; U.S. Pat. Publ. No. US2009/0182127; U.S. Pat. Publ. No. US2010/0286374; U.S. Pat. Publ. No. US2011/0123532; Int. Pat. Publ. No. WO2011/131746; Int. Pat. Publ. No. WO2011/143545; or U.S. Pat. Publ. No. US2012/0149876. Additional bispecific structures into which the VL and/or the VH regions of the antibodies of the invention can be incorporated are for example Dual Variable Domain Immunoglobulins (Int. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. No. 5,932,448; U.S. Pat. No. 6,833,441).

Another aspect of the invention is an isolated polynucleotide encoding any of the antibody heavy chain variable regions or the antibody light chain variable regions or fragments thereof of the invention or their complement. Given the degeneracy of the genetic code or codon preferences in a given expression system, polynucleotides encoding the antibody antagonists of the invention are also within the scope of the invention.

Another embodiment of the invention is a vector comprising the polynucleotide of the invention. Such vectors may be plasmid vectors, viral vectors, vectors for baculovirus expression, transposon based vectors or any other vector suitable for introduction of the polynucleotides of the invention into a given organism or genetic background by any means.

Another embodiment of the invention is a host cell comprising the polynucleotide of the invention. Such host cells may be eukaryotic cells, bacterial cells, plant cells or archeal cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

Another embodiment of the invention is a method of producing an antibody of the invention comprising culturing a host cell of the invention and recovering the antibody produced by the host cell. Methods of making antibodies and purifying them are well known in the art.

Another embodiment of the invention is a method of inhibiting interaction of IFNω and IFNα subtypes IFNαB2, IFNαF, IFNαG and/or IFNαJ1 with IFNAR in a patient need thereof, comprising administering an isolated antibody that competes for binding to the human IFNω and the human IFNα subtypes IFNαB2, IFNαF, IFNαG and/or IFNαJ1 with an isolated antibody comprising: a heavy chain variable region (VH) of SEQ ID NO: 23 and a light chain variable region (VL) of SEQ ID NO: 24; or a VH of SEQ ID NO: 27 and a VL of SEQ ID NO: 28 to a patient for a time sufficient to prevent the interaction of IFNω and IFNα subtypes IFNαB2, IFNαF, IFNαG and/or IFNαJ1 with IFNAR. Competition between an antibody and IFNAR can be assayed using standard methods and those described herein using for example extracellular portions of IFNAR1 (SEQ ID NO: 31) and IFNAR2 (SEQ ID NO: 32) or their Fc fusion proteins.

Methods of Treatment

IFNα/ω antibodies of the invention may be utilized to treat or prevent any disease that is associated with increased production of IFNα and IFNω. In the methods of the invention, any IFNα/ω antibody of the invention may be used. Alternatively, any antibody competing for binding to the human IFNω and the human IFNα subtypes IFNαB2, IFNαF, IFNαG and/or IFNαJ1 with an isolated antibody comprising: a heavy chain variable region (VH) amino acid sequence of SEQ ID NO: 23 and a light chain variable region (VL) amino acid sequence of SEQ ID NO: 24; or a VH amino acid sequence of SEQ ID NO: 27 and a VL amino acid sequence of SEQ ID NO: 28 may be used. Further, any antibody that binds IFNω at one or more residues F27, L30 and R33 of SEQ ID NO: 1 and IFNα4a at one or more residues F27, L30 and R33 of SEQ ID NO: 19 may be used.

The methods of the invention may be used to treat an animal patient belonging to any classification. Examples of such animals include mammals such as humans, rodents, dogs, cats and farm animals. For example, the antibodies of the invention are useful in the prophylaxis and treatment of immune-mediated inflammatory diseases, such as systemic lupus erythematosus (SLE), type I diabetes, psoriasis, primary Sjögren's disease, systemic sclerosis, rheumatoid arthritis, inflammatory bowel disease (IBD; including Crohn's Disease, Ulcerative Colitis and Celiac's Disease), immune-mediated inflammatory thyroiditis, and glomerulonephritis. Furthermore, the antibody compositions of the invention can be used for inhibiting or preventing transplant rejection or in the treatment of graft versus host disease (GVHD).

The antibodies of the invention are also useful in the preparation of a medicament for such treatment, wherein the medicament is prepared for administration in dosages defined herein.

Not wishing to be bound by any particular theory, it is suggested that SLE triggers, such as immune complexes, invoke type I IFN responses including IFNα and IFNω, but not IFNβ. Therefore, IFNα/ω antibodies of the invention may provide a more efficacious SLE treatment broadly inhibiting these pathogenic Type I IFNs, while sparing IFNβ function, which may play a more critical role in antiviral defense. In the present invention, broadly neutralizing IFNα/ω antibodies have been generated and a unique neutralizing epitope present on IFNα and IFNω identified, albeit the challenges given the suggestion that IFNα and IFNω are antigenically unique (Adolf, J Gen Virol 68:1669-1676, 1987.

A relationship between IFNα and SLE was first described in 1979 when this cytokine was demonstrated to be elevated in the serum of SLE patients (Hooks et al., N Engl J Med 301:5-8, 1979; Preble et al., Science 216:429-431, 1982). More recently, a type I IFN gene signature has been extensively described in a subset of SLE patients and the extent of IFN signature expression has been reported to positively correlate with both clinical and serological features of disease (Karageorgas et al., J Biomed Biotechnol 273907, 2011; Baechler et al., Proc Natl Acad Sci USA 100:2610-2615, 2003; Bennett et al., J Exp Med 197:711-723, 2003; Dall'era et al., Ann Rheum Dis 64: 1692-1697, 2005; Niewold et al., Genes Immun 8: 492-502, 2007). Several genetic association studies have indicated a potential role for the type I IFN pathway in mediating disease in some lupus patients (Delgado-Vega et al., Arthritis Res Ther 12 Suppl 1 S2; Elkon and Stone; J Interferon Cytokine Res 11:803-812, 2011). Further studies have revealed that IFNα modulates the expression of a suite of gene products involved with pathogenic mechanisms in SLE. For example, IFNα can induce the expression of BLyS an important B cell survival factor and also the target of Benlysta® (belimumab). A positive correlation exists with type I IFN activity and levels of soluble BLyS in SLE patients (Ritterhouse et al., Arthritis Rheum 63:3931-3941, 2011), and blockade of IFNα in SLE patients resulted in a decrease in the gene expression of BLyS in skin lesional biopsies of a small number of SLE patients where tissue was collected (Yao et al., Arthritis Rheum 60:1785-1796, 2009). In concert with IL-6, IFNα was also shown to be important for the generation of Ig-secreting plasma cells (Jego et al., Curr Dir autoimmune 8:124-139, 2005). Outside of direct effects on the B-cell compartment, IFNα exhibits effects on other important mediators of lupus pathogenesis. Blanco et al. demonstrated that IFNα can induce the differentiation of monocytes to antigen-presenting DCs (Blanco et al., Science 294:1540-1543, 2001). Neutralization of IFNα present in SLE serum samples significantly reduced the capacity of SLE serum to induce monocyte to DC differentiation demonstrating a prominent role of this cytokine in decreasing tolerance to self antigens in some SLE patients. IFNα therapy for infectious or oncologic indications has been shown to induce SLE-like disease in some patients, which subsides after therapy is discontinued (Burdick et al., Expert Opin Drug Saf 8:459-472, 2009; Biggioggero et al., Autoimmunity 43:248-254, 2010).

IFN is rapidly produced in response to infectious agents such as viruses to help control infection. Autoantibodies bound to nucleic acid ligands are thought to be the predominant inducers of type I IFN in SLE. A preponderance of autoantibodies in conjunction with an impaired clearance of autoantigens leads to a feedback cycle of IFN production where Fc receptor-dependent internalization of immune complexes into plasmacytoid dendritic cells (pDC) leads to increased amounts of IFN and thus establishment of the IFN signature. Nucleic acid receptors such as toll-like receptors (TLR) 7 and TLR9 are enriched in the endosomal compartment of pDCs and considered to be predominant sentinels of these nucleic acid-containing immune complexes initiating a cascade leading to type I IFN release. To that end, multiple inhibitors of TLRs 7 and 9 are in clinical development for SLE.

Both IFNα and IFNω are elevated in SLE and may induce similar immunomodulatory effects. Agonism of TLR7 and TLR9 using synthetic ligands (Gibson et al., Cell Immunol 218:74-86, 2002) or SLE patient-derived immune complexes (as described herein) induced both IFNα and IFNω protein IFNω transcripts (Han et al., Genes Immun 4:177-186, 2003) and protein (data not shown) are upregulated in SLE patients.

Autoantibodies against type I IFN are also found in SLE patients, possibly as a result of elevated IFN in these patients coupled with an over exuberant humoral immune response. Autoantibodies against IFNω have been found to be more prevalent than those against IFNα in the SLE cohorts examined while only trace amounts of autoantibodies against IFNβ were detected (Slavikova et al., J Interferon Cytokine Res 23:143-147, 2003). General activities conferred by IFNω resemble IFNα effects suggesting that elevated IFNω in SLE patients may contribute to disease pathogenesis (Adolf et al., J Biol Chem 265:9290-9295, 1990; Adolf, Mult Scler 1 Suppl 1:S44-47, 1995; Kubes et al., J Interferon Res 14:57-59, 1994; Tiefenthaler et al., J Interferon Cytokine Res 17:327-329, 1997). The presence and role of IFNβ in SLE is less certain. Specific neutralization of IFNα using SLE patient sera as stimuli resulted in a substantial reduction of type I IFN activity while IFNβ neutralization conferred negligible effects using the patient sera samples tested, suggesting minimal involvement of IFNβ to disease pathogenesis (Hua et al., Arthritis Rheum 54:1906-1916, 2006).

Current type I IFN antagonist approaches in clinical development are focused on neturalizing a spectrum of IFNα subtypes and not other type I IFNs (β, ε, κ, ω), on neutralizing the IFNAR1 chain of the interferon receptor thus blocking signal transduction of all type I IFN, or utilizing vaccination approaches specific to IFNα (Merrill et al., Ann Rheum Dis 70:1905-1913, 2011; Zagury et al., Proc Natl Acad Sci USA 106:5294-5299, 2009). In clinical trials, anti-IFNα antibodies in SLE patients demonstrated partial reduction of the type I IFN signature in patients exhibiting the IFN signature and slight efficacy in exploratory analysis (Merrill et al., Ann Rheum Dis 70:1905-1913, 2011). In Phase 2 studies, anti-INFα treatment in the absence of immunosuppressants was associated with improvement in signs and symptoms of SLE, flare rates, and steroid burden at week 24 in a pre-specified biomarker defined group of Interferon Signature Metric (ISM)-Low moderate to severely active lupus subjects. Interestingly, no efficacy was seen in patients pre-defined as ISM-High (Kalunian et al., 2012 ACR/ARHP Annual Meeting; Abstract #2622, 2012).

A monoclonal antibody against IFNAR1 would be predicted to abolish IFN signaling induced by all type I IFNs, including IFNβ. Despite a lack of data to support a significant role of IFNβ in SLE pathogenesis, IFNβ may play a more critical role in antiviral defense. Specific deletion of the gene encoding IFNβ incurs substantial susceptibility to a host of viruses when compared to similarly exposed mice having functional IFNβ (Lazear et al., J Virol 85:7186-94; Deonarain et al., J Virol 74:3403-09, 2000; Deonarain et al., Circulation 110:3540-3543, 2004; Gerlach et al., J Virol 80:3438-3444, 2006; Koerner et al., J Virol 81:2025-2030, 2007).

One embodiment of the invention is a method of treating or preventing a disease associated with increased production of IFNα and IFNω, comprising administering a therapeutically effective amount of an isolated antibody that binds to and neutralizes activity of human interferon omega (IFNω) and at least four, five, six, seven, eight, nine or ten human interferon alpha (IFNα) subtypes, or an antibody that competes for binding to the human IFNω and the human IFNα subtypes IFNαB2, IFNαF, IFNαG or IFNαJ1 with an isolated antibody comprising: a heavy chain variable region (VH) amino acid sequence of SEQ ID NO: 23 and a light chain variable region (VL) amino acid sequence of SEQ ID NO: 24; or a VH amino acid sequence of SEQ ID NO: 27 and a VL amino acid sequence of SEQ ID NO: 28 to a patient in need thereof for a time sufficient to treat or prevent the disease.

Another embodiment of the invention is a method of preventing interaction of IFNω and IFNα subtypes IFNαB2, IFNαF, IFNαG or IFNαJ1 with IFNAR in a patient need thereof, comprising administering an isolated antibody that binds to and neutralizes activity of human interferon omega (IFNω) and at least four, five, six, seven, eight, nine or ten human interferon alpha (IFNα) subtypes, or an antibody that competes for binding to the human IFNω and the human IFNα subtypes IFNαB2, IFNαF, IFNαG and/or IFNαJ1 with an isolated antibody comprising: a heavy chain variable region (VH) amino acid sequence of SEQ ID NO: 23 and a light chain variable region (VL) amino acid sequence of SEQ ID NO: 24; or a VH amino acid sequence of SEQ ID NO: 27 and a VL amino acid sequence of SEQ ID NO: 28 to a patient for a time sufficient to prevent the interaction of IFNω and IFNα subtypes IFNαB2, IFNαF, IFNαG and/or IFNαJ1 with IFNAR. In other embodiments, the antibody that may be used in the methods of the invention comprises an antibody that binds IFNω at one or more residues F27, L30 and R33 of SEQ ID NO: 1 and IFNα4a at one or more residues F27, L30 and R33 of SEQ ID NO: 19.

The antibodies of the invention may be tested for their efficacy in animal models of lupus, which include strains of lupus-prone mice and mice in which lupus-like phenotypes are induced or accelerated using various agents (Perry, et al., J Biomed Biotechnol, 2011:271694, 2011. For example, NZB/NZW F1 mice exhibit a time-dependent and female-biased disease having several features of human lupus including glomerulonephritis. As multiple and distinct IFNα subtypes are produced in the mouse when compared to human (van Pesch, et al., J Virol, 78:8219-28, 2004) and lack of IFNω expression in mouse, in vitro testing in disease relevant cells using disease relevant IFN preparations may be used to assess the efficacy and disease modifying potential of the antibodies of the invention. Such in vitro assays are for example evaluation of inhibition of IFN production induced by SLE Immune Complex in whole blood, or assessment of ability of the antibodies to reduce the IFN signature as described herein.

The VH and the VL domains of the IFNα/ω antibodies of the invention of may be incorporated into bispecific antibodies and molecules described herein, in which the bispecific antibody specifically binds and neutralizes IFNω and at least four, five, six, seven, eight, nine or ten human interferon alpha (IFNα) subtypes, for example IFNαB2, IFNαF, IFNαG and IFNαJ1, and a second antigen such as BLyS, CD40L, IL-6, CD27, BDCA2 (CLEC4C, C-type lectin domain family 4, member C), or p40 subunit of IL-12 and IL-23. Alternatively, the VH and the VL domains of any antibody competing for binding to the human IFNω and the human IFNα subtypes IFNαB2, IFNαF, IFNαG and/or IFNαJ1 with an isolated antibody comprising: a heavy chain variable region (VH) amino acid sequence of SEQ ID NO: 23 and a light chain variable region (VL) amino acid sequence of SEQ ID NO: 24; or a VH amino acid sequence of SEQ ID NO: 27 and a VL amino acid sequence of SEQ ID NO: 28 may be used. Further, the VH and the VL domains of any antibody that binds IFNω at one or more residues F27, L30 and R33 of SEQ ID NO: 1 and IFNα4a at one or more residues F27, L30 and R33 of SEQ ID NO: 19 may be used.

BLyS, CD40L, IL-6, CD27, BDCA2 (CLEC4C, C-type lectin domain family 4, member C), or p40 subunit of IL-12 and IL-23 binding antibodies can be generated using methods described herein, such as immunizing mice expressing human immunoglobulin loci (Lonberg et al., Nature 368: 856-9, 1994; Fishwild et al., Nature Biotechnology 14:845-51, 1996; Mendez et al., Nature Genetics 15:146-56, 1997, U.S. Pat. Nos. 5,770,429, 7,041,870, and 5,939,598) or Balb/c mice with the corresponding proteins or extracellular domains of the proteins, or using phage display libraries as described herein. Alternatively, existing antibodies to BLyS, CD40L, IL-6, CD27, BDCA2 (CLEC4C, C-type lectin domain family 4, member C) or p40 subunit of IL-12 and IL-23 can be used to generate the bispecific molecules.

Administration/Pharmaceutical Compositions

The "therapeutically effective amount" of the IFNα/ω antibodies of the invention effective in the treatment of conditions associated with increased production of IFNα and IFNω can be determined by standard research techniques. For example, the dosage of the IFNα/ω antibodies of the invention that will be effective in the treatment of immune-mediated inflammatory diseases such as SLE can be determined by administering the IFNα/ω antibodies to relevant animal models well known in the art.

In vitro assays can optionally be employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems. The antibodies of the invention may be tested for their efficacy and effective dosage using any of the models described herein.

The mode of administration for therapeutic use of the antibody of the invention may be any suitable route that delivers the agent to the host. Pharmaceutical compositions of these antibodies are particularly useful for parenteral administration, e.g., intradermal, intramuscular, intraperitoneal, intravenous, subcutaneous, or intranasal.

The antibody of the invention may be prepared as pharmaceutical compositions containing an effective amount of the agent as an active ingredient in a pharmaceutically acceptable carrier. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibody of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected.

Thus, a pharmaceutical composition of the invention for intramuscular injection could be prepared to contain 1 ml sterile buffered water, and between about 1 ng to about 100 mg, e.g. about 50 ng to about 30 mg or more preferably, about 5 mg to about 25 mg, of an antibody of the invention. Similarly, a pharmaceutical composition of the invention for intravenous infusion could be made up to contain about 250 ml of sterile Ringer's solution, and about 1 mg to about 30 mg and preferably 5 mg to about 25 mg of an antagonist of the invention. Actual methods for preparing parenterally administrable compositions are well known and are described in more detail in, for example, "Remington's Pharmaceutical Science", 15th ed., Mack Publishing Company, Easton, Pa.

The antibodies of the invention can be lyophilized for storage and reconstituted in a suitable carrier prior to use. This technique has been shown to be effective with conventional immunoglobulins and protein preparations and art-known lyophilization and reconstitution techniques can be employed.

Further Embodiments of the Invention

Set out below are certain further numbered embodiments of the invention according to the disclosures elsewhere herein. Features from embodiments of the invention set out above also relate to each and every one of these further numbered embodiments.

1) An isolated monoclonal antibody that binds to and neutralizes an activity of (a) human interferon omega (IFNω) and (b) at least four, five, six, seven, eight, nine or ten human interferon alpha (IFNα) subtypes.
2) The antibody according to embodiment 1, wherein the antibody binds to and neutralizes an activity of the human IFNα subtypes IFNαB2, IFNαF, IFNαG and IFNαJ1.
3) The antibody according to embodiment 1 or 2, wherein the antibody binds to and neutralizes an activity of the human IFNα subtypes IFNαB2, IFNαC, IFNαF, IFNαG and IFNαJ1.
4) The antibody according to any one of embodiments 1-3, wherein the antibody binds to and neutralizes an activity of the human IFNα subtypes IFNαB2, IFNαC, IFNαF, IFNαG, IFNαJ1 and IFNαA.
5) The antibody according to any one of embodiments 1-4, wherein the antibody binds to and neutralizes an activity of the human IFNα subtypes IFNαB2, IFNαC, IFNαF, IFNαG, IFNαJ1, IFNαA and IFNαH2.
6) The antibody according to any one of embodiments 1-5, wherein the antibody binds to and neutralizes an activity of the human IFNα subtypes IFNαB2, IFNαC, IFNαF, IFNαG, IFNαJ1, IFNαA, IFNαH2 and IFNαK.
7) The antibody according to any one of embodiments 1-6, wherein the antibody binds to and neutralizes an activity of the human IFNα subtypes IFNαB2, IFNαC, IFNαF, IFNαG, IFNαJ1, IFNαA, IFNαH2, IFNαK and IFNαWA.
8) The antibody according to any one of embodiments 1-7, wherein the antibody binds to and neutralizes an activity of the human IFNα subtypes IFNαB2, IFNαC, IFNαF, IFNαG, IFNαJ1, IFNαA IFNαH2, IFNαK, IFNαWA and IFNα4a.
9) The antibody according to any one of embodiments 1-8, wherein the activity of the human IFNω and the human IFNα subtypes is inhibition of secreted embryonic alkaline phosphatase (SEAP) expression under the interferon inducible ISG54 promoter in HEK293 cells stably expressing signal transducer and activator of transcription 2 (STAT2), interferon regulatory factor 9 (IRF9) and SEAP.
10) The antibody according to any one of embodiments 1-9, wherein the antibody inhibits the activity of the human IFNω with an $IC_{50}$ value of about $5\times10^{-8}$ M or less, about $1\times10^{-8}$ M or less, about $1\times10^{-9}$ M or less, about $1\times10^{-10}$ M or less, about $1\times10^{-11}$ M or less or about $1\times10^{-12}$ M or less, and inhibits the activity of the human IFNα subtypes IFNαB2, IFNαF, IFNαG or IFNαJ1 with an $IC_{50}$ value of about $5\times10^{-8}$ M or less, about $1\times10^{-8}$ M or less, about $1\times10^{-9}$ M or less, about $1\times10^{-10}$ M or less, about $1\times10^{-11}$ M or less or about $1\times10^{-12}$ M or less under conditions defined in Example 3 under section "affinity measurements".
11) The antibody according to any one of embodiments 1-10, wherein the antibody binds the human IFNω with a dissociation constant ($K_D$) of about $5\times10^{-9}$ M or less, about $1\times10^{-9}$ M or less, about $5\times10^{-10}$ M or less, about $1\times10^{-10}$ M or less, about $5\times10^{-11}$ M or less, about $1\times10^{-11}$ M or less, about $5\times10^{-12}$ M or less or about $5\times10^{-12}$ M or less and binds the human IFNα subtypes IFNαB2, IFNαF, IFNαG or IFNαJ1 with a $K_D$ of about $5\times10^{-9}$ M or less, about $1\times10^{-9}$ M or less, about $5\times10^{-10}$ M or less, about $1\times10^{-10}$ M or less, about $5\times10^{-11}$ M or less, about $1\times10^{-11}$ M or less, about $5\times10^{-12}$ M or less or $5\times10^{-12}$ M or less, wherein the $K_D$ is measured using conditions exemplified in Example 3 under section "affinity measurements."

12) The antibody according to any one of embodiments 1-11, wherein the antibody competes for binding to the human IFNω and the human IFNα subtypes IFNαB2, IFNαF, IFNαG and/or IFNαJ1 with an isolated antibody comprising:
   a) a heavy chain variable region (VH) amino acid sequence of SEQ ID NO: 23 and a light chain variable region (VL) amino acid sequence of SEQ ID NO: 24; or
   b) a VH amino acid sequence of SEQ ID NO: 27 and a VL amino acid sequence of SEQ ID NO: 28.
13) The antibody according to any one of embodiments 1-12, wherein the antibody binds IFNω at one or more of residues F27, L30 and R33 of SEQ ID NO: 1.
14) The antibody according to any one of embodiments 1-13, wherein the antibody binds IFNω at residues F27, L30 and R33 of SEQ ID NO: 1.
15) The antibody according to any one of embodiments 1-14, wherein the antibody further binds at least one IFNω residue selected from the group consisting of residues P26, K31 and R34 of SEQ ID NO: 1.
16) The antibody according to embodiment 14 or 15, wherein the antibody further binds at least one IFNω residue selected from the group consisting of residues R22, R23, I24, S25, P26, K31, D32, R34, D35, Q40, K134, M146, E147, M149, K150, F153 and L154 of SEQ ID NO: 1.
17) The antibody according to any one of embodiments 1-16, wherein the antibody binds IFNα4a at one or more of residues F27, L30 and R33 of SEQ ID NO: 19.
18) The antibody according to any one of embodiments 1-17, wherein the antibody binds IFNα4a at residues F27, L30 and R33 of SEQ ID NO: 19.
19) The antibody according to embodiment 17 or 18, wherein the antibody further binds at least one IFNα4a residue selected from the group consisting of residues H26, K31 and R34 of SEQ ID NO: 19.
20) The antibody according to any one of embodiments 17-19, wherein the antibody further binds at least one IFNα4a residue selected from the group consisting of A19, G22, R23, I24, S25, H26, C29, K31, D32, H34, D35, V143, A146, E147, M149, R150 and S153 of SEQ ID NO: 19.
21) The antibody according to any one of embodiments 1-20, wherein the antibody inhibits activity of viral-induced leukocyte interferon.
22) The antibody according to embodiment 21, wherein the activity of viral-induced leukocyte interferon is IP-10 release in whole blood induced by 100 U/ml of interferon.
23) The antibody according to embodiment 22, wherein the activity is inhibited by more than 50% in the presence of 50 µg/ml antibody.
24) The antibody according to any one of embodiments 1-23, wherein the antibody inhibits activity of systemic lupus erythematosus (SLE) immune complex-induced IFN.
25) The antibody according to embodiment 24, wherein the activity is inhibited by more than about 50%.
26) The antibody according to any one of embodiments 1-25, comprising:
   a) a heavy chain variable region (VH) amino acid sequence of SEQ ID NO: 23 and a light chain variable region (VL) amino acid sequence of SEQ ID NO: 24; or
   b) a heavy chain variable region (VH) amino acid sequence of SEQ ID NO: 27 and a light chain variable region (VL) amino acid sequence of SEQ ID NO: 28.
27) The antibody according to any one of embodiments 1-26, wherein the antibody does not bind or neutralize human interferon-β (IFNβ).
28) The antibody according to any one of embodiments 1-27, wherein the antibody does not bind or neutralize human IFNαD.
29) The antibody according to any one of embodiments 1-28, wherein the antibody is human, humanized or human-adapted.
30) The antibody according to any one of embodiments 1-29, wherein the antibody is of IgG1, IgG2, IgG3 or IgG4 isotype.
31) The antibody according to any one of embodiments 1-30, wherein the antibody is bispecific.
32) The antibody according to embodiment 31, wherein the antibody binds BLyS, CD40L, IL-6, CD27, BDCA2 or the p40 subunit of IL-12 or IL-23.
33) A pharmaceutical composition comprising the antibody according to any one of embodiments 1-32 and a pharmaceutically accepted carrier.
34) The antibody according to any one of embodiments 1-32 or the pharmaceutical composition according to embodiment 33 for use in the treatment or prevention of a disease associated with increased production of IFNα and/or IFNω.
35) The antibody according to any one of embodiments 1-32 or the pharmaceutical composition according to embodiment 33 for use according to embodiment 34, wherein the disease associated with increased production of IFNα and/or IFNω is an immune-mediated inflammatory disease, optionally wherein the immune-mediated inflammatory disease is systemic lupus erythematosus (SLE), type I diabetes, psoriasis, primary Sjögren's disease, systemic sclerosis or rheumatoid arthritis.
36) The antibody according to any one of embodiments 1-32 or the pharmaceutical composition according to embodiment 33 for use according to embodiment 34 or 35, wherein the patient exhibits a Type I interferon signature.
37) The antibody according to any one of embodiments 1-32 or the pharmaceutical composition according to embodiment 33 for use according to embodiment 34-36, wherein the antibody is a bispecific antibody, optionally wherein the bispecific antibody binds BLyS, CD40L, IL-6, CD27, BDCA2 or the p40 subunit of IL-12 or IL-23.
38) The antibody according to any one of embodiments 1-32 or 37 or the pharmaceutical composition according to embodiment 33 for use in inhibiting interaction of IFNω and IFNα subtypes IFNαB2, IFNαC, IFNαF, IFNαG and/or IFNαJ1 with IFNAR in a patient.
39) The antibody or the pharmaceutical composition for use according to embodiment 38, wherein the patient has an immune-mediated inflammatory disease, optionally wherein the immune-mediated inflammatory disease is SLE, type I diabetes, psoriasis, primary Sjögren's disease, systemic sclerosis or rheumatoid arthritis.
40) The antibody or the pharmaceutical composition for use according to embodiment 38 or 39, wherein the patient exhibits a Type I interferon signature.
41) The antibody or the pharmaceutical composition for use according to any one of embodiment 38-40, wherein the antibody is a bispecific antibody, optionally wherein the bispecific antibody binds BLyS, CD40L, IL-6, CD27, BDCA2, p40 subunit of IL-12 or IL-23, or BDCA2.

The present invention will now be described with reference to the following specific, non-limiting examples.

Example 1 Generation of Human Type I IFN
Antigens Used for Immunization, Phage Panning,
Antibody Characterization, and Crystallography
Studies Twelve individual recombinant human type I IFN alphas, including Alpha A (alpha 2a) (SEQ ID NO: 5), Alpha B2 (alpha 8) (SEQ ID NO: 6), Alpha C (alpha 10) (SEQ ID NO: 7), Alpha D (alpha 1) (SEQ ID NO: 8), Alpha F (alpha 21) (SEQ ID NO: 9), Alpha G (alpha 5) (SEQ ID NO: 10), Alpha H2 (alpha 14) (SEQ ID NO: 11), Alpha I (alpha 17) (SEQ ID NO: 12), Alpha J1 (alpha 7) (SEQ ID NO: 13), Alpha K (alpha 6) (SEQ ID NO: 14), Alpha 4b (alpha 4) (SEQ ID NO: 15), Alpha WA (alpha 16) (SEQ ID NO: 16) and chimpanzee IFN omega (chimp IFNω) (SEQ ID NO: 3) were expressed in HEK 293 cells using standard methods using signal sequences, such as SEQ ID NOs: 17-21. To improve expression level and solubility, a single amino acid mutant at position 80 of human IFN omega IFN-omega (T80E) was generated and expressed in HEK 293 cells. The T80E IFNω variant (SEQ ID NO: 2) had comparable activity to the wild type protein.

Example 2. Generation of IFNα and IFNω Binding
and Neutralizing Antibodies Mouse Immunizations Generation of C2595

BALB/c mice were immunized intraperitoneally multi times with mixture of human IFN-alphas, chimpanzee IFN-omega and cynomolgus IFN-omega. On day 0, mice were immunized with chimpanzee IFN-omega. On day 14, the same mice were immunized with mixture of chimpanzee and cynomolgus IFNomega, human IFNαD, IFNαJ1, IFNαC, IFNαB2, IFNαH2, IFNαA, IFNα4a, IFNαG, IFNαF, IFNαWA and IFNαI. On day 208, the same mice were immunized with mixture of cynomolgus IFN-omega, human IFNα4b, IFNαA, IFNαD, and IFNαK. On day 221, the same mice were immunized with mixture of cynomolgus IFN-omega, human IFNαJ, IFNαI, IFNα4a, IFNαA and IFNαF. Specific IgG titers were assessed after immunization. Once sufficient titers were obtained, splenocytes were isolated and fused with FO cells. The resulting hybridomas were plated in 96 well plates and cultured for 10 days. Antigen specific clones were first identified by primary screen for binding of chimpanzee IFN-omega and binding of mixture of human IFNαA, IFNαH2, IFNαD, and IFNα4a with ELISA. Hybridomas binding to IFN-alpha and/or IFN-omega were further screened by Luminex multiplex assay. Clones binding broadly to most of IFN alphas and human and cyno IFN omega were selected for further studies.

Phage Display Libraries

Human type I IFN binding Fabs were selected from de novo pIX phage display libraries described in Shi et al., J. Mol. Biol. 397:385-396, 2010; Int. Pat. Publ. No. WO2009/085462; U.S. Pat. Publ. No. US2010/0021477; U.S. Pat. Publ. No. US2012/0108795.

Selection of IFWM43

The pIX phage display libraries were panned against purified type I IFN alpha A (IFNα2) generated from the expression of human wild-type IFN-alpha A sequence a C-terminal poly-histidine tag and purified by immobilized metal affinity chromatography. Three round panning was used. The 100 nM, 10 nM and 1 nM of biotinylated antigen were used for first, second and third round panning respectively. The monoclonal Fabs derived from phagemid clones harvested after three round panning were primary screened for their binding chimp IFN omega, human IFNα2, IFNα1, IFNαH2, IFNαG, IFNα F and avidin with a standard ELISA. The Fab fragments (Fabs) that bound specifically to IFN alphas and IFN-omega in ELISA were sequenced and identified as unique IFN binders if they have different Vregion sequences. The Fabs were converted to human IgG1 mAb and identified as IFN binders after further tested their neutralizing activity in a range of cell-based assays relevant to identifying anti-inflammatory activity.

Identification of IFWM88

The pIX phage display libraries were panned against purified type I IFN alpha G (a5) generated from the expression of human wild-type IFN-alpha A sequence a C-terminal poly-histidine tag and purified by immobilized metal affinity chromatography. Three round panning was used. The 100 nM, 10 nM and 1 nM of biotinylated antigen were used for first, second and third round panning respectively. The monoclonal Fabs derived from phagemid clones harvested after three round panning were primary screened for their binding chimp IFN omega, human IFNα2, IFNα1, IFNαH2, IFNαG, IFNαF and avidin with a standard ELISA. The Fab fragments (Fabs) that bound specifically to IFN alphas and IFN-omega in ELISA were sequenced and identified as unique IFN binders if they have different V region sequences. The Fabs were converted to human IgG1 mAbs and identified as IFN binders after further testing their neutralizing activity in a range of cell-based assays relevant to identifying anti-inflammatory activity.

Amino acid sequences of variable regions of generated antibodies are as follows: IFWM43 VH: SEQ ID NO: 23; IFWM43 VL: SEQ ID NO: 24; and IFWM88 VH: SEQ ID NO: 25; IFWM88 VL: SEQ ID NO: 26; C2595 VH: SEQ ID NO: 27, C2494 VL: SEQ ID NO: 28. C2595 variable regions were transferred to human IgG1 constant region and the resulting antibody was named M3239. IFWM43 is also referred to as M43 and IFWM88 is referred to as M88.

Example 3. Characterization of IFN-α and IFN-ω
Binding and Neutralizing Antibodies Methods Affinity Measurements Binding affinities of the antibodies were performed using SPR technology with ProteOn™ XPR36 (protein interaction array system) (Bio-Rad Hercules, Calif.). Goat anti-human Fc antibodies (manufacture) were amine-coupled to GLC chips (Bio-Rad Hercules, Calif.) using standard NHS/EDC chemistry as manufacture recommended. The anti-IFN mAbs were then loaded on the antibody coupled chip for 2 minutes at the flow rate of 30 µl/min. After washing with running buffer (composition of the buffer) for 2 minutes at the flow rate of 50 µl/ml, recombinant IFN antigens at 5 different concentrations ranging from 100 nM to 1.23 nM with 1:3 dilution were allowed to associate for 3 minutes and dissociate for 10 minutes, both at the flow rate of 50 µl/ml. The chips were generated with 100 mM phosphoric acid in each direction between running different antigens. Data analysis was performed using ProteOn™ XPR36 (protein interaction array system) manager (Bio-Rad Hercules, Calif.). The sensorgrams were grouped by mAbs. After applying alignment and reference correction (using either interspot or blank channel referencing), the SPR data were fit globally to Langmuir model for kinetic rate constants ($K_D = k_{off}/k_{on}$, where $K_D$=equilibrium dissociation constant, $k_{on}$=association rate constant, and $k_{off}$=dissociation rate constant).

ISRE Reporter Gene Assay ("ISRE Reporter Gene Assay")

HEK-Blue™ IFN-α/β cells (InvivoGen, San Diego, Calif.) engineered to express a fully active type I IFN signaling pathway (stably expressing STAT2 and IRF9) and transfected with a SEAP reporter gene under the control of the IFN-α/β inducible ISG54 promoter was used. The cells were grown in collagen type I coated T150 flasks in Dulbecco's modified eagle media with 10% fetal bovine serum, 100 ug/ml blasticidin and 30 ug/ml zeocin at 37° C., 5% $CO_2$. Cells were harvested and plated in 384-well plates at 50 µl per well at 50,000 cells per ml. Plated cells were incubated at 37° C., 5% $CO_2$ for 24 hr. Tested interferon samples were prepared and diluted in spent HEK ISRE serum free medium, and 50 µl of IFN sample was added to each well. Plated cells were incubated at 37° C., 5% $CO_2$ for 20 hr. Alkaline phosphatase was detected from 20 µl of plated cell supernatants with 60 µl/well QUANTI-Blue™ resuspended in filtered water after incubation for 20 min at room temperature. Optical density was read on a Biotek Synergy plate reader at 650 nm.

Some ISRE reporter gene assays were done in 96-well plates as follows: HEK-Blue™ IFN-α/β cells (InvivoGen, San Diego, Calif.) were plated at 50,000 cells per well in 100 µl of selection free media (DMEM+Glutamax/10% FBS, Gibco) and allowed to incubate overnight at 37° C. The next day, type I IFN stimuli were prepared (i.e. recombinant interferon, leukocyte IFN, IC induced IFN preps, serum, etc) with or without type I IFN inhibitors in a separate 96 well U-bottom transfer plate (BD Falcon) and prewarmed at 37° C. for 10 minutes. A plate of cells was removed from incubator and media was removed and replaced with 100 µl of appropriate treatments prepared in 96 well U-bottom transfer plate. Cells were placed back at 37° C. for 24 hours. The next day, 40 µl of supernatant was transferred to a 96 well flat bottom plate (BD Falcon) containing 160 µl of QUANTI-Blue™ SEAP substrate (Invivogen). Plate was allowed to develop for about 15 minutes at which time it was read using a spectrometer at an absorbency of 650 nm.

IP-10 Release Assay:

Heparinized whole blood from healthy volunteers was plated in a 96 well U-bottom plate containing several different type I IFN inhibitors along with isotype controls. Inhibitors and appropriate isotype control were diluted in RPMI medium with 10% FBS. IFNs and inhibitors or isotype controls were diluted in a volume of 30 µl of RPMI Medium containing 10% FBS. After pre-incubating the samples for 15-20 minutes 240 µl of heparinized whole blood was added to plates containing the dilutions to make a final volume of 270 µl. Samples were mixed and allowed to incubate at 37° C. for 20-22 hours. After incubations, samples were spun at 400×g for 5 minutes and plasma was collected and frozen for later analysis. IP-10 profiling was done by Milliplex cytokine/chemokine kit (Millipore, Premixed 39 plex. Sample preparation and assay were performed according to the manufacturer's recommendation using BioRad model (Bioplex™ 200) system and Bioplex Manager™ software 4.1 to acquire the data. Statistical analysis was done by Graph pad Prism V.5 software. In some cases, IP-10 was quantified using Single analyte ELISA kit from Qiagen.

SLE Whole Blood Gene Signature Assay:

SLE donor whole blood was obtained commercially through Asterand. Whole blood gene expression analysis was performed using a custom TaqMan low density array card containing primers and probes enriched for IFN-stimulated genes (ISGs). Genes included on the array were as follows: ACTB, IL6, IL10, IL13, FAS, IL15, IL21, IL17A, EIF2AK2, OASL, 18S, STAT1, LY6E, PLSCR1, MX1, IFIT1, IF144, IF144L, IF127, ISG15, RSAD2, CXCL10, LAG3, and TNFSF10. RT-PCR amplification was performed on an ABI Prism 7900 HT Sequence Detection system (Applied Biosystems, CA, USA) as per manufacturer's instructions. Relative expression values were calculated using the comparative threshold cycle ($C_t$) method. Briefly, this technique uses the formula $2^{-\Delta\Delta C}t$ to calculate the expression of target genes normalized to a calibrator group (Normal healthy untreated whole blood). Beta Actin (ACTB) was selected as the endogenous control. The threshold cycle ($C_t$) indicates the cycle number by which the amount of amplified target reaches a fixed threshold. The Q data for all interferon-induced target genes and ACTB were used to create $\Delta C_t$ values [$\Delta C_t = C_t(\text{target gene}) - C_t(\text{ACTB})$]. $\Delta\Delta C_t$ values were calculated by subtracting the average of the control group (5 normal healthy untreated whole blood donors) from the $\Delta C_t$ value of each target. Relative expression values were calculated using the equation $2^{-\Delta\Delta C}$. The 3 SLE donors in this experiment had a minimum of 2 fold higher gene expression over the control group for 9 of the ISGs on the low density array. To compare the effects of the type I IFN inhibitors across all 3 donors, % inhibition was first determined using the following formula for every treatment/inhibitor: ($2^{-\Delta\Delta C}t$ SLE blood untreated$-2^{-\Delta\Delta C}t$ inhibitor/$2^{-\Delta\Delta C}t$ SLE blood untreated)×100=% inhibition. Next, % baseline for each treatment across all three donors was calculated by the following equation: 100−% inhibition=% baseline.

The mean % baseline of all 3 donors grouped by treatment groups was then determined for each of the 9 genes. The untreated SLE group ("SLE blood alone") was set to 100 to denote that this group is 100% from the baseline. Baseline denotes that there is 0% IFN-induced gene expression. Finally, the mean and standard deviation of each treatment group across all 9 genes was determined and plotted. Statistical significance was determined by performing the Student's T-test.

SLE Immune Complex Preparation:

SLE patient plasma was obtained from SCIPAC (Kent, UK). Plasma samples having type I IFN activity as determined by an ISRE-based reporter gene assay were further utilized for IgG purification. IgG was purified using NAB™ Protein A/G Spin column as recommended by the manufacturer (Thermo SCIENTIFIC) and protein assay was run to determine concentration (Pierce BCA). Autoantigen lysates were prepared using HEK293T cells suspended at $5×10^7$ cells/ml in 1× phosphate buffered saline (PBS). To disrupt Hek293T cells, freeze-thawing was performed for 4 cycles of at least 10 minutes freezing at −80° C. and thawing at 37° C., except for an initial freezing of at least 30 minutes; after the freeze-thaw, cellular debris was removed by centrifugation (400 g for 5 minutes) and soluble antigen amount was quantitated by protein assay. At a 1:1 ratio, purified IgG and necrotic cell lysate was incubated together for 30 minutes at RT to form immune complexes. A final concentration of 400 µg/ml of immune complex was then added to 3 wells of a 6 well plate in a total volume of 4 ml PBMC media per well. Healthy donor IgG was purified and "complexed" in the same manner just described and used to stimulate PBMCs to serve as a control. Conditioned media from these studies was aliquoted and used as a source for endogenous IFN for inhibition experiments. No IFN activity was seen with preps prepared from IgG isolated from healthy volunteers.

Results
Affinity to and Neutralization of Recombinant Type I IFNs

Table 2 shows dissociation constants ($K_D$) of antibodies M43, M88 and M3239 to individual recombinant human type I interferons (IFNs). M43, M88 and C2595 neutralized at least four IFNα molecules: alphaB2, alphaF, alphaG and alphaJ1. No binding was observed for alphaD.

Table 3 shows the $IC_{50}$ values for antibodies M43, M88 and M3239 (C2595) to individual recombinant human type I IFNs measured in a reporter gene assay. M43 was broadly neutralizing, inhibiting at least 10 IFNα molecules. M3239 neutralized IFNω with a sub pM $IC_{50}$ while M43 neutralized IFNω with an $IC_{50}$ in nM range. M88 did not demonstrate neutralizing activity towards IFNω in the specific assay due to its very weak binding of it. However, after affinity maturation, the antibodies derived from M88 showed strong IFNω neutralizing activity while retaining their broad IFNα neutralizing activities (data not shown). None of the antibodies bound or neutralized IFNβ.

TABLE 2

| | Antibody $K_D$ (nM) | | |
|---|---|---|---|
| Antigen | M43 | M88 | M3239 |
| IFNαA | 0.1 | 14.9 | NB |
| IFNαB2 | 0.9 | 0.3 | 32.2 |
| IFNαC | 0.4 | 3.2 | 1.3 |
| IFNαD | NB | NB | NB |
| IFNαF | 0.9 | 1 | 15.1 |
| IFNαG | 0.6 | 0.8 | 10.3 |
| IFNαH2 | 0.6 | 5.5 | 61.6 |
| IFNαJ1 | 0.4 | 4.5 | 4.3 |
| IFNαK | 0.3 | ND | NB |
| IFNαI | ND | ND | ND |
| IFNαWA | 0.6 | 97.3 | NB |
| IFNα4a | 1.7 | 23.3 | NB |
| IFNβ | 8 | NB | NB |
| IFNω | 0.3 | 53 | 4.5 |

NB = no binding
ND: not tested
M3239: human/mouse chimeric IgG1 derived from c2595

TABLE 3

| | Antibody $IC_{50}$ (nM) | | |
|---|---|---|---|
| Antigen | M43 | M88 | C2595 |
| IFNαA | 0.1 | NA | NA |
| IFNαB2 | 25.9 | 25.2 | 11.1 |
| IFNαC | 14.9 | 136.1 | 1.5 |
| IFNαD | NA | NA | NA |
| IFNαF | 3.7 | 24.6 | 2.6 |
| IFNαG | 5.3 | 23.4 | 2.6 |
| IFNαH2 | 51 | PA | 20.3 |
| IFNαJ1 | 1 | 21.9 | 1.4 |
| IFNαK | 10.4 | NA | NA |
| IFNαI | ND | ND | ND |
| IFNαWA | 9.2 | NA | NA |
| IFNα4a | 8.1 | 218.6 | NA |
| IFNβ | NA | NA | NA |
| IFNω | 18.5 | NA | 0.9 |

NA: no neutralizing activity
PA: partial neutralizing activity
ND: not tested

Neutralization of Endogenous Type I IFN

Figure 1B:
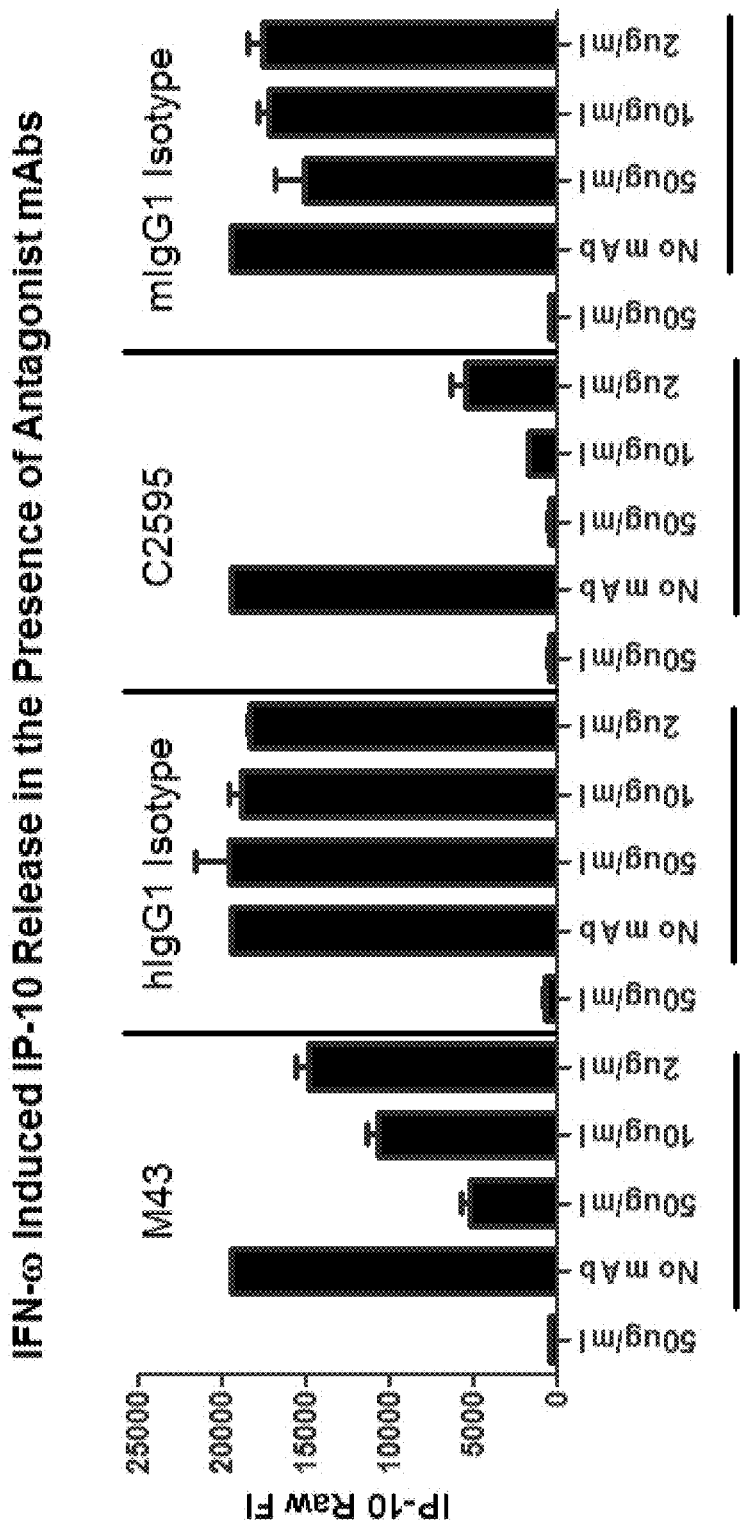

The ability of the antibodies to neutralize endogenous Type I IFN was assessed in an assay evaluating the release of the chemokine IP-10 (CXCL10) from human whole blood stimulated with endogenous leukocyte IFN (viral induced) or recombinant IFNω. Dose-dependent inhibition of both leukocyte IFN (FIG. 1A) and recombinant IFNω (FIG. 1B) was seen with M43 and C2595 indicating the ability of the antibodies to neutralize activity of a wide spectrum of type I such as those produced by virally induced leukocytes. The endogenous leukocyte IFN was purchased from Sigma (catalogue number #I4784-1MU).

Neutralization of Disease Associated IFN Mileu

Figure 2:
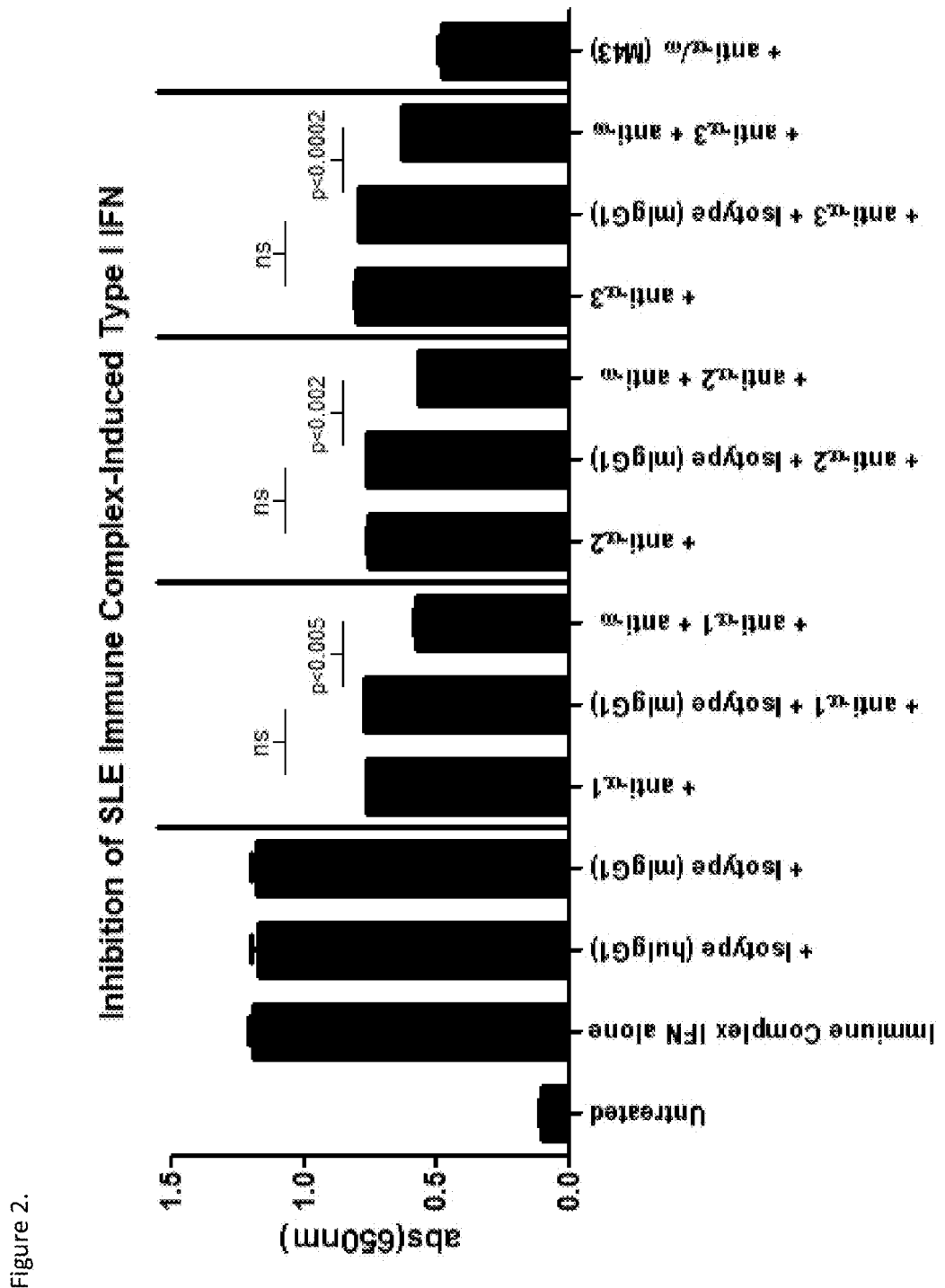

Antibodies were tested for their ability to reduce SLE immune complex-induced IFN as stimulus to better represent the type I IFN milieu present in SLE. SLE immune complex-induced IFN was prepared by stimulating human PBMCs with SLE patient-derived immune complexes and this conditioned media was utilized in a type I IFN-inducible reporter gene assay (ISRE reporter gene assay as described above) in the presence of inhibitor mAbs and control mAbs. The addition of a selective IFNω neutralizing mAb in combination with 3 different IFNα antagonist mAbs further reduced the total activity of immune complex-induced IFN in comparison to the anti IFNα mAbs in the presence of an equivalent amount of isotype control mAb (FIG. 2). Furthermore, anti IFNα/ω mAb M43 demonstrated further suppression of activity in comparison to IFNα inhibitor mAbs suggesting that dual blockade of IFNα and IFNω can reduce more total IFN activity than IFNα neutralization alone (FIG. 2).

IFNω Contributes to SLE Associated IFN Mileu

Figure 3:
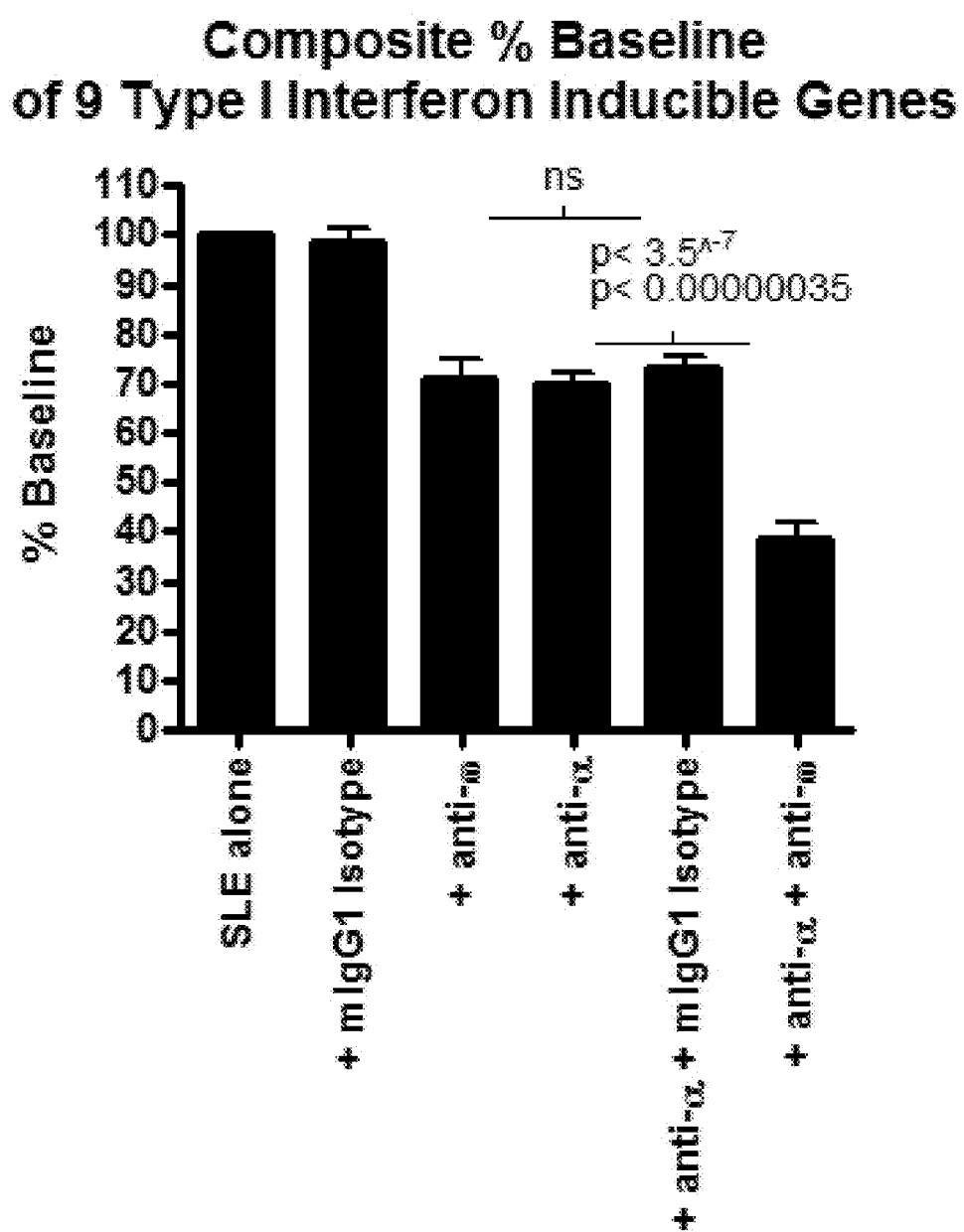

An assay for the SLE gene signature was developed as described above utilizing a combination of nine IFN-induced genes. The ability of various antibodies to inhibit the gene signature was tested. An IFNω specific antagonist mAb (anti-ω) downmodulated the IFN signature in comparison to an equivalent concentration of isotype control mAb, suggesting that IFN-ω is part of the active type I IFN milieu that induces an IFN signature in SLE. The combination of an IFNω antibody with an IFNα antibody resulted in more pronounced suppression of the IFN signature perpetuated in the blood of these patients than an IFNα or IFNω inhibitor alone (FIG. 3).

Example 4. Competitive Epitope Mapping

Epitope binding experiments were performed using real-time label-free competitive binding assays using Octet (ForteBio, Menlo Park, Calif.). Two assay formats were used: the in tandem assay format and the classic sandwich assay format.

In the in tandem assay format streptavidin biosensor tips (forteBio, Menlo Park, Calif.) were dipped into 0.5 mg/ml biotinlyted recombinant interferon for 5 minutes while the real-time kinetic signal was measured. Then the tips were dipped into the first set of mAbs (10 μg/ml) for 15 minutes. The tips were subsequently dipped into the second set of mAbs (10 μg/ml) for another 10 or 15 minutes. The positive binding signal from the tips dipped into the second set of mAbs shows their binding to different epitopes from the first set of mAbs and negative signal shows their binding to the same epitopes. To eliminate the false results due to the affinity difference of two sets of mAbs, the experiment were repeated with the reverse order, that is the tips were dipped into second set of mAbs first and then into first set of mAbs. All the antibodies and antigens were diluted into PBS with 1 mg/ml BSA and 0.02% Tween 20.

In the classic sandwich assay format the first set of mAbs were coupled on the amine reactive biosensor tips using standard NHS/EDC-mediated chemistry following manufacture's protocol (forteBio, Menlo Park, Calif.). After quenching for 5 minutes in ethanolamine, the tips were dipped into recombinant interferons (2 μg/ml) for 10 minutes before they were dipped into the 2nd set of mAbs (15 μg/ml) for 10 or 15 minutes. The coupling mAbs were diluted in MES buffer 6.0 while the binning mAbs and the antigens were diluted into PBS with 1 mg/ml BSA and 0.02% Tween 20.

Three epitope binning experiments were performed using both assay formats using the following antibodies: M43, M88 and C2595 (binding multiple IFNα subtypes and IFNω), C2601 and M42 (binds IFNω but weakly to IFNα subtypes), and C2605 (binding multiple IFNα subtypes but not IFNω). Various IFN-α molecules were tested in the competition assay (human IFNα subtypes IFNαA, IFNαB, IFNαC, IFNαF, IFNαG, IFNαH, IFNαJ, IFNα2, IFNα4a, as well as chimp IFNω and human IFNAR2-Fc molecule.

Table 4 shows the results of competition in the presence of M43 and Table 5 shows the competition in the presence of IFNAR2-Rc. M43 and M88 competed with each other for binding to all tested IFNα molecules and chimp IFNω. M42, which does not bind to IFNω did not compete for binding to the tested IFN-molecules with M43. M43 competed with C2595 and IFNAR-Fc for binding to chimp IFNω and various IFNα molecules. C2605 did not compete with binding with M43 to most IFNα, indicating that the two antibodies bind a different epitope. C2601, a strong IFNω binder but weak IFNα binder did not compete with binding with M43 to IFNω with M43, indicating the two antibodies bind a distinct epitope. C2595 but not C2601 or C2605 competed with binding to chimp IFNω and/or IFNαA with IFNAR2-Fc. The antibodies that bind IFNω and multiple IFNα subtypes and therefore define distinct epitope bins as follows: BinA: mabs M43, M88, C2595. Antibodies that bind only IFNα or IFNω form distinct epitope bin(s).

Example 5. Epitope of M43 Derived from the Crystal Structure of Anti-IFNα/ω Antibody M43 in Complex with IFNα T80E Mutant IFWM43 (hereafter M43 and FabM43 for mAb and Fab, respectively) broadly neutralizes human IFNα molecules and IFNα and shows binding to a number of IFNα subtypes and human IFNω. In order to reveal the structural basis for its specificity to IFNα subtypes and IFNω the crystal structure of the IFN-ω in complex with FabM43 was determined Materials and Methods Proteins The His-tagged FabM43 (IgG1/κ isotype) and a human IFNω with T80E mutation (in this example IFNω and IFNωT80E are synonymous) were expressed in HEK293F cells and purified using affinity and size-exclusion chromatography. The proteins were in 20 mM Tris pH 7.4, 50 mM NaCl.

Crystallization of IFNω/FabM43 Complex

The complex was prepared by mixing of IFNω with FabM43 in molar ratio of 1.05:1.0 (excess IFNω), purified over Superdex™ 200 size exclusion chromatography media column equilibrated with 20 mM Na acetate, pH 5.5, 0.1 M NaCL and 10% glycerol. The purified complex was concentrated to 10.24 mg/ml using Amicon-Ultra 10 kDa cutoff. Crystals suitable for X-diffraction were obtained in sitting drops from 0.1 M MES, pH 6.5, 26% PEG 3350, 1 M LiCL, 0.7% 1-butanol with MMS seeding as described (Obmolova et al., Acta Crystallogr D Biol Crystallogr 66:927-33, 2010).

X-Ray Data Collection and Structure Determination

For X-ray data collection, crystals were soaked for a few seconds in the synthetic mother liquor (0.1 MES pH 6.5, 20% PEG 3350, 1 M LiCL) supplemented with 20% glycerol, and flash frozen in liquid nitrogen. X-ray diffraction data were collected at Swiss Light Source. The X-ray data were processed with the program XDS (Kabsch, Acta Crystallographica 66:125-132, 2010). X-ray data statistics are given in Table 6.

The structure was solved by molecular replacement (MR) with Phaser (Read, Acta Crystallogr D Bio Crystallogr 57:1373-82, 2001). The search models for MR were the crystal structure of Fab15 (PDB ID 3NCJ; Luo et al., J Mol Biol 402:708-719, 2010) and IFN-α2 (PDB ID 1RH2; Radhakrishnan et al., Structure 4:1453-1463, 1996)), the Cα model of which was available in the PDB. To use for MR, the complete molecular model of IFN-α2 was obtained by MR using Phaser with the Cα coordinates and reflection data

TABLE 4

| | Antibody or receptor fusion protein | | | | | | |
|---|---|---|---|---|---|---|---|
| Antigen | M80 | M88 | M42 | C2595 | C2601* | C2605** | IFNaR2-Fc |
| IFNαA | − | NT | + | − | + | ++ | − |
| IFNαB | NT | − | NT | − | − | − | − |
| IFNαC | NT | − | NT | − | − | ++ | − |
| IFNαF | NT | − | NT | − | + | ++ | − |
| IFNαG | NT | − | + | − | − | ++ | − |
| IFNαH | − | − | + | − | − | ++ | − |
| IFNαJ | NT | − | NT | − | − | ++ | − |
| IFNα2 | − | NT | NT | − | + | ++ | − |
| IFNα4a | NT | − | NT | − | − | ++ | − |
| chimp IFNω | − | − | NT | − | ++ | − | − |

"−" indicates no binding
"+" or "++" indicated binding
NT: not tested
*c2601 does not bind to IFNaA with high affinity
**c2605 does not bind to chimp IFNw

TABLE 5

| | Antigen | |
|---|---|---|
| Antibody | Chimp IFNω | IFNαA |
| C2595 | — | — |
| C2601 | ++ | —* |
| C2605 | —** | ++ |

* c2601 does not bind to IFNaA with high affinity
** c2605 does not bind to chimp IFNw in the PDB, and refined with PHENIX (Adams et al., J Syncrhrotron Radiat 11:53-55, 2004). The IFN-ω/FabM43 structure was refined using PHENIX and model adjustments were carried out using COOT (Emsley and Cowtan, Acta Crystallogr D Biol Crystallogr 60:2126-2132, 2004). All other crystallographic calculations were performed with the CCP4 suite of programs (Collaborative Computational project, Acta Crystallogr D Biol Crystallogr 53:240-255, 1994). The elbow angle between the variable and constant domains was calculated with the program RBOW (Stanfield et al., J Mol Biol 357:1566-1574, 2006). Molecular graphics were generated with PyMol (DeLano, Palo Alto, Calif., USA, Delano-Scientific). The structure refinement statistics are given in Table 6.

TABLE 6

Crystal data and refinement statistics.

X-ray diffraction data

| | |
|---|---|
| Space group | P2$_1$ |
| Unit cell dimensions | |
| a, b, c (Å) | 132.20, 107.35, 142.48 |
| α, β, γ (°) | 90, 101.96, 90 |
| Asymmetric unit content | 6 complexes |
| Resolution (Å) | 50.00-2.50 (2.56-2.50) [d] |
| No. measured reflections | 357,014 (3,854) [d] |
| No. unique reflections | 110,299 (1,929) [d] |
| Completeness (%) | 82.1 (19.1) [d] |
| Redundancy | 3.2 (2.0) [d] |
| R-merge [a] | 0.085 (0.404) [d] |
| <I/σ> (avg) | 10.0 (2.1) [d] |
| B-factor (Wilson) (Å$^2$) | 51.3 |

Refinement

| | |
|---|---|
| Resolution (Å) | 48.50-2.50 (2.58-2.50) |
| R$_{cryst}$/R$_{free}$(%) [b] | 23.4/27.7 (36.3/49.9) |
| No. of reflections | |
| Working/Test set | 109,900/1,610 |
| Number of atoms | |
| Proteins | 27,056 |
| Solvent (water, etc.) | 1,228 |
| RMSD bond lengths (Å) | 0.004 |
| RMSD bond angles (°) | 0.76 |
| Mean B-factors (Å$^2$) | |
| Protein | 35.9 |
| Solvent | 36.2 |
| Ramachandran plot [c] | |
| Favored regions (%) | 96.4 |
| Outliers (%) | 0.4 |

[a] R$_{merge}$ = Σ|I − <I>|/ΣI, where I is the intensity of the measured reflection and <I> is the mean intensity of all measurements of this reflection.
[b] R$_{cryst}$ = Σ ||F$_{obs}$| − |F$_{calc}$||/Σ |F$_{obs}$|, where F$_{obs}$ and F$_{calc}$ are observed and calculated structure factors and R$_{free}$ is calculated for a set of randomly chosen 5% of reflections prior to refinement.
[c] The Ramachandran plot was calculated with MolProbity.
[d] The anisotropic resolution limits in a*, b* and c* are 3.0, 2.5 and 2.5 Å, according to the diffraction anisotropy scale server (http://_services_mbi_ucla.edu/_anisoscale/). Diffraction data statistics are for the dataset after anisotropic truncation and scaling using these limits.

Results the Overall Structure

Figure 4:
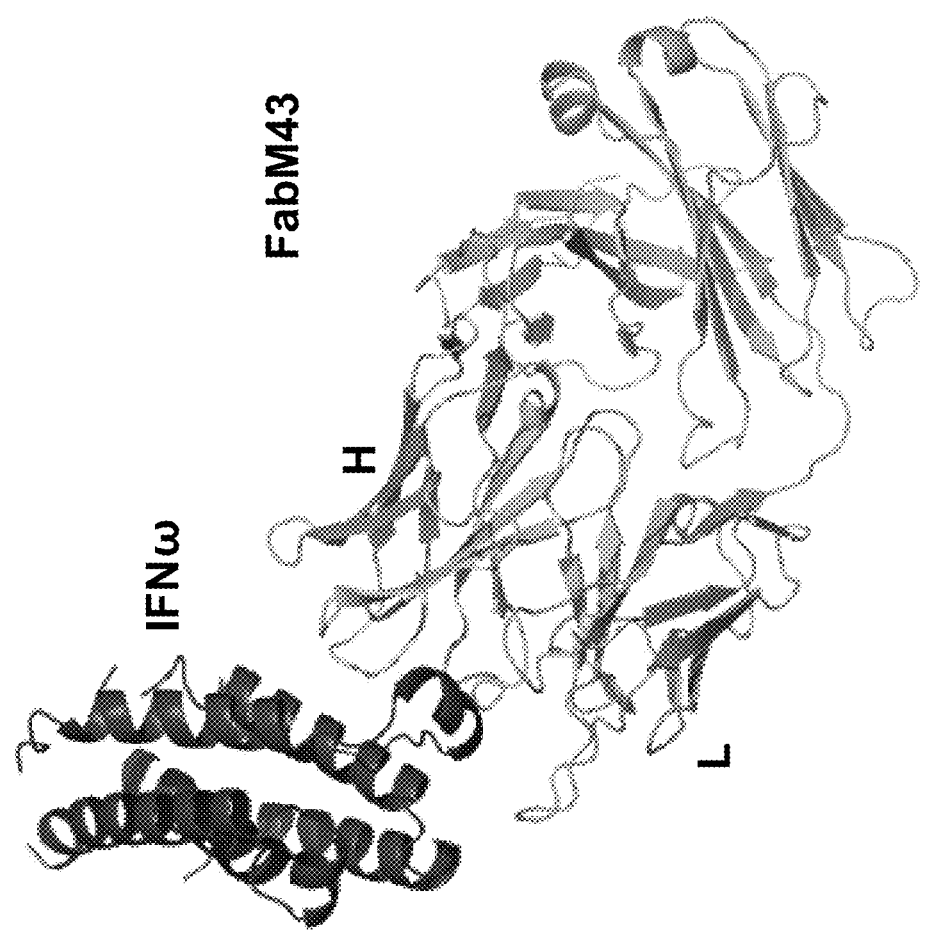

There are six IFNω/FabM43 complexes in the asymmetric unit. All of these complexes are very similar. The overall representative molecular structure of the IFNω/FabM43 complex is shown in FIG. 4. In the Figure: marked H is VH; marked L is VL, top left is IFNω

The IFNω molecules have essentially identical conformation with an average Cα rmsd of less than 0.35 Å. The molecular structure of IFNω is a helix bundle that is very similar to IFN-α2 with an average Cα rmsd of 0.53 Å and almost identical to the published IFN-ω (pdb id 3se4) with Cα rmsd of 0.47 Å and IFNβ (Cα rmsd 0.85 Å for 94 residues). However, there are some significant differences between IFNα/ω and IFN-β because the IFNβ AB loop is one residue shorter. The Fab molecules also have identical structures except for a short stretch in CDR-H1 (G$_{26}$GTF$_{29}$) (SEQ ID NO: 33), which adopts slightly different backbone conformations.

the Epitope, Paratope and Ab/Ag Interactions

M43 recognizes a conformational epitope that is composed of residues of the AB loop (between R22 and Q40) and residues K134, M146, M149, K150, F153 and L154 of helix E (Table 7). The paratope is composed of residues from five of the six CDRs. The paratope residues are mainly hydrophobic, which form a series of pockets into which dock the side chains of residues F27, L30, K31 and R33 of the short AB helix. The antibody and antigen interactions appear to be mostly vdw and hydrophobic packing. There are only a small number of H bonds between the antibody and antigen, and most of them involve backbone-backbone or sidechain-backbone interactions. Several residues F27, L30, K31 and R33 of the AB helix account for the majority of the Ab/Ag interactions. Thus, this region of IFNω appears to constitute the main part of the epitope.

TABLE 7

Epitope and paratope of antibody M43. Contact residues for all six complexes are shown. Residue numbering according to human IFNω SEQ ID NO: 1

| | ABO | CDP | EFQ | GHR | IJX | KJT |
|---|---|---|---|---|---|---|
| VL: | Y31 | Y31 | Y31 | Y31 | Y31 | Y31 |
| | S33 | S33 | S33 | S33 | S33 | S33 |
| | Y38 | Y38 | Y38 | Y38 | Y38 | Y38 |
| | F98 | F98 | F98 | F98 | F98 | F98 |
| | D99 | D99 | D99 | D99 | D99 | D99 |
| | Y102 | Y102 | Y102 | Y102 | Y102 | Y102 |
| VH: | | | | T28 | | |
| | F29 | F29 | F29 | F29 | F29 | F29 |
| | S30 | S30 | S30 | | | |
| | S31 | S31 | S31 | S31 | S31 | S31 |
| | | Y32 | Y32 | | | Y32 |
| | A33 | A33 | A33 | A33 | A33 | A33 |
| | G50 | G50 | G50 | G50 | G50 | G50 |
| | | | | I51 | | |
| | I52 | | I52 | I52 | I52 | I52 |
| | I54 | I54 | | | | |
| | F55 | F55 | F55 | F55 | F55 | F55 |
| | T57 | T57 | T57 | T57 | T57 | T57 |
| | A58 | A58 | A58 | A58 | A58 | A58 |
| | N59 | N59 | N59 | N59 | N59 | N59 |
| | D99 | D99 | D99 | D99 | D99 | D99 |
| | W101 | W101 | W101 | W101 | W101 | W101 |
| | Y105 | Y105 | Y105 | Y105 | Y105 | Y105 |
| IFN-ω | R22 | R22 | R22 | | | R22 |
| | P26 | P26 | P26 | P26 | P26 | P26 |
| | F27 | F27 | F27 | F27 | F27 | F27 |
| | L30 | L30 | L30 | L30 | L30 | L30 |
| | K31 | K31 | K31 | K31 | K31 | K31 |
| | D32 | D32 | D32 | D32 | D32 | D32 |
| | R33 | R33 | R33 | R33 | R33 | R33 |
| | R34 | R34 | R34 | R34 | R34 | R34 |
| | D35 | D35 | D35 | D35 | D35 | D35 |
| | Q40 | | Q40 | Q40 | Q40 | Q40 |
| | K134 | K134 | K134 | K134 | K134 | K134 |
| | M146 | M146 | M146 | M146 | M146 | M146 |
| | M149 | M149 | M149 | | | M149 |
| | K150 | K150 | K150 | K150 | | K150 |
| | F153 | F153 | F153 | F153 | F153 | F153 |
| | L154 | L154 | L154 | L154 | L154 | L154 |

All residues within 3.9 Å of the binding partners are considered contact residues.
Antibody VL and VH residues are numbered sequentially.

Mode of Antibody Neutralization

The crystal structure of IFNα/ω in complex with IFNAR1 and/or IFNAR2 has recently been reported (Thomas et al., Cell 146:621-632, 2011). Comparing the M43/IFNα4 structure and IFNω/IFNAR1/IFNAR2 complex indicates clearly that M43 heavy chain and IFNAR2 would overlap. Thus, M43 neutralizes by blocking IFNAR2/IFN interactions.

Example 6. Epitope of C2595 from the Crystal Structures of Fab357 (Fab of C2595) in Complexes with IFNωT80E or IFNα4A C2595 (hereafter C2595 and Fab357 for mAb and Fab, respectively) is an antibody that neutralizes multiple human IFN-α molecules and IFNω obtained from mouse hybrodima. The V regions were cloned and chimerized onto human heavy and light chains (IgG1κ isotype) to produce the recombinant Fab357. The crystal structures of the IFN-ω/Fab357 and IFN-α4A/Fab357 complexes were determined Materials and Method
Proteins The His-tagged Fab357 (IgG1/κ isotype) and a human IFNω with T80E mutation (hereafter IFNωT80E. IFNω and IFNω with T80E are synonymous in this example) were expressed in HEK293F cells and purified using affinity, and size-exclusion chromatography. The proteins were in 20 mM Tris pH 7.4, 50 mM NaCl.). IFNα4A was obtained from Crown Bioscience Inc. in 20 mM Tris pH 7.4, 50 mM NaCl.

Crystallization of IFNα4A/Fab357 and IFNω/Fab357 Complexes

The IFNα4A/Fab357 complex were prepared by mixing of IFNα4A with Fab357 in molar ratio of 1.05:1.0, and purified over a Superdex™ 200 size exclusion chromatography media column in 20 mM MES pH 6.5 with 0.1 M NaCL. The purified complex was concentrated to 5.5 mg/ml. Diffraction quality crystal were grown in sitting drops composed of equal mixture of the protein solution and 20% PEG 3350 and 0.2 M ammonium citrate with seeding.

The IFNω/Fab357 complex was prepared by mixing of IFNω with Fab357 in molar ratio of 1.17:1.0 (excess IFNω), incubated at 4° C. for 2 hr, and the IFNω/Fab357 complex was purified on Superdex™ 200 size exclusion chromatography media column (GE Healthcare) equilibrated with 20 mM HEPES pH 7.5, 0.1 M NaCL and concentrated to 6.8 mg/ml. Crystals suitable for X-diffraction were obtained from sitting drops composed of equal mixture of the protein complex and 100 mM MES pH 6.5, 18% PEG 3K, 0.2 M LiCl with seeding.

X-Ray Data Collection and Structure Determination

For X-ray data collection, crystals of IFNα4A/Fab357 and IFNω/Fab357 were soaked for a few seconds in the synthetic mother liquors (20% PEG 3350, 0.2 M Ammonium citrate, Plate 10/20/11-MMS-A10; 0.1 MES pH 6.5, 18% PEG 3350, 0.2 M LiCL, Plate 12/21/2011-B11(R), respectively) supplemented with 20% glycerol, and flash frozen in liquid nitrogen. The X-ray diffraction data were collected at Advance Photon Source of Argonne National Lab and Swiss Light Source, respectively. The X-ray data were processed with the program XDS. X-ray data statistics are given in Table 8.

The structures were solved by molecular replacement (MR) with Phaser. The search models for MR were the crystal structure of Fab 15 (PDB ID 3NCJ) and IFNω in the complex with M43. The structures were refined using PHENIX[5] and model adjustments were carried out using COOT. All other crystallographic calculations were performed with the CCP4 suite of programs. Molecular graphics were generated with PyMol. The structure refinement statistics are given in Table 8.

TABLE 8

Crystal data and refinement statistics.

| X-ray diffraction data | IFNα4A/Fab357 | IFNω/Fab357 |
|---|---|---|
| Space group | P6₅22 | C222₁ |
| Unit cell dimensions | | |
| a, b, c (Å) | 156.07, 156.07, 122.81 | 70.23, 104.33, 155.38 |
| α, β, γ (°) | 90, 90, 120 | 90, 90, 90 |
| Asymmetric unit content | 1 complex | 1 complex |
| Resolution (Å) | 50.00-2.30 (2.36-2.30) | 50.00-2.20 (2.26-2.20) |
| No. measured reflections | 260,405 (19,875) | 193,190 (13,207) |
| No. unique reflections | 39,577 (2,888) | 29,394 (2,143) |
| Completeness (%) | 99.9 (100.0) | 99.9 (99.9) |
| Redundancy | 6.6 (6.9) | 6.6 (6.2) |
| R-merge $^a$ | 0.059 (0.618) | 0.056 |
| <I/σ> (avg) | 20.0 (3.3) | 0.539 |
| B-factor (Wilson) (Å²) | 45.2 | 45.2 |
| Refinement | | |
| Resolution (Å) | 39.30-2.30 (2.36-2.30) | 43.31-2.20 (2.26-2.20) |
| $R_{cryst}/R_{free}$(%) $^b$ | 19.3/23.6 (25.4/31.1) | 20.0/25.0 (22.1/28.3) |
| No. of reflections | | |
| Working/Test set | 37,572/1,998 | 27,390/2,000 |
| Number of atoms | | |
| Proteins | 4,555 | 3,785 |
| Solvent (water, etc.) | 198 | 180 |
| RMSD bond lengths (Å) | 0.008 | 0.005 |
| RMSD bond angles (°) | 1.12 | 0.95 |
| Mean B-facors (Å²) | | |
| Protein | 48.4 | 45.6 |
| Solvent | 42.3 | 43.3 |
| Ramachandran plot $^c$ | | |
| Favored regions (%) | 96.2 | 96.5 |
| Outliers (%) | 0.4 | 0.2 |
| All atom Clashscore | 9.8 | 8.9 |

$^a$ $R_{merge} = \Sigma|I - <I>|/\Sigma I$, where I is the intensity of the measured reflection and <I> is the mean intensity of all measurements of this reflection.

$^b$ $R_{cryst} = \Sigma||F_{obs}| - |F_{calc}||/\Sigma |F_{obs}|$, where $F_{obs}$ and $F_{calc}$ are observed and calculated structure factors and $R_{free}$ is calculated for a set of randomly chosen 5% of reflections prior to refinement.

The Ramachandran plot was calculated with MolProbity.

Results
the Overall Structure

Figure 5:
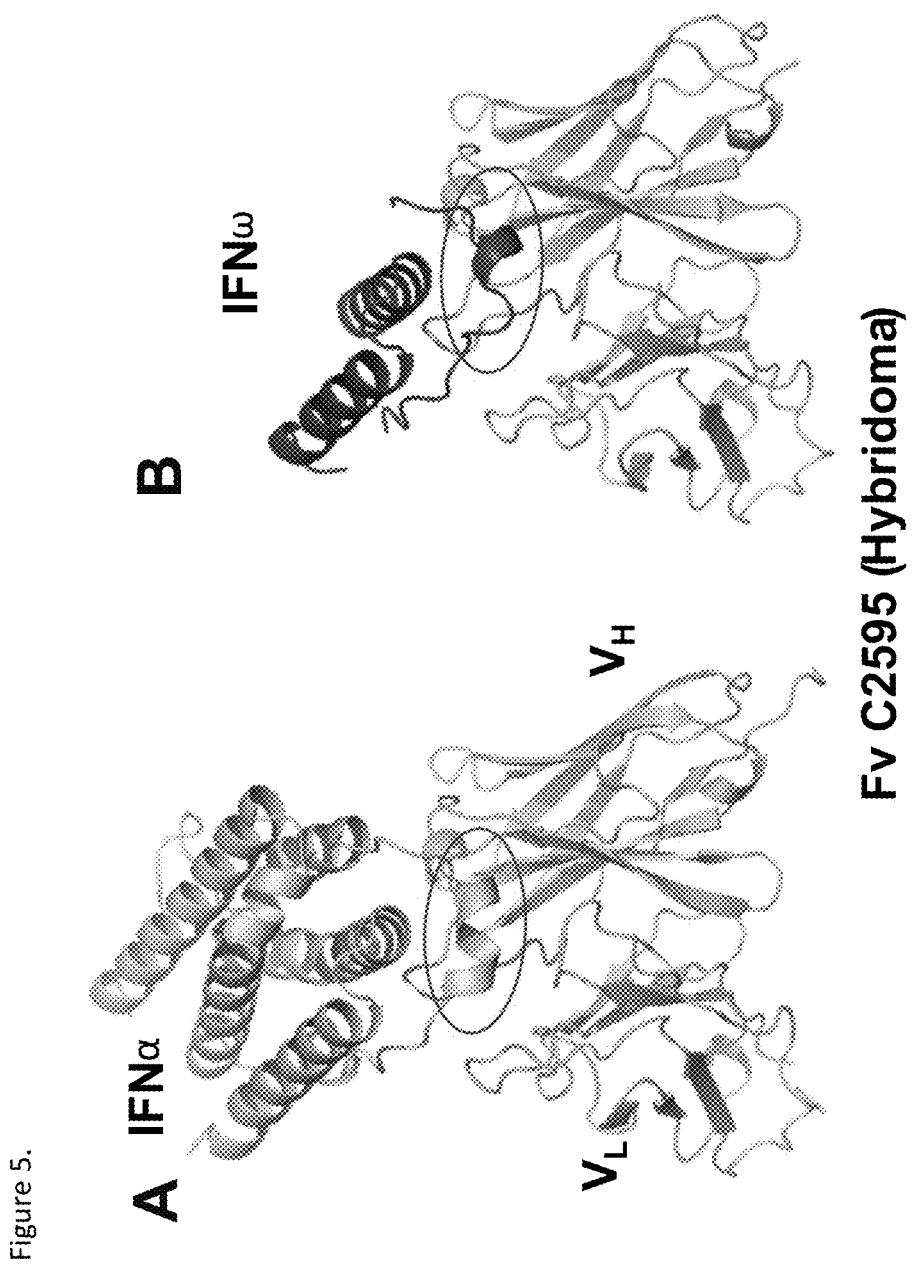

There is one antigen/antibody complex in the asymmetric unit in both crystal structures. The overall representative molecular structures are shown in FIG. 5. The Fab molecule is very similar in both crystals. The IFNα4A conformation is very similar to that in IFNα4A/FabM88. For the IFNω/Fab357 structure, the IFNω model includes only residues R22-P39 and L118-L154. The missing residues of IFNω are not a result of disorder in the crystal because crystal packing precludes their presence. Apparently, proteolytic cleavage of IFNω occurred during crystallization. There was evidence that part of the same complex sitting in the cold box had suffered some protease degradation, though the pattern was not identical to what was identified in the crystal (data not shown). Nevertheless, the binding regions of IFNω were well ordered.

The Epitope, Paratope and Ab/Ag Interactions

C2595 recognizes a nearly identical conformational epitope on both IFNα4A and IFNω that is composed of residues of the AB loop (between R/G22 and R/H34) and residues V143, M/A146, E147 and R/K150 of helix E (Table 9). The paratope is composed of residues from four of the six CDRs (CDR-L1, L3, H2 and H3). The paratope residues are mainly hydrophobic, which form a series of pockets into which dock the side chains of residues F27, L30, K31 and R33 of the short AB helix. The antibody and antigen interactions appear to be mostly vdw and hydrophobic packing. There are only a small number of H bonds between the antibody and antigen, and most of them involve backbone-backbone or sidechain-backbone interactions. Several residues F27, L30, K31 and R33 of the AB helix account for the majority of the Ab/Ag interactions. Thus, this region of IFNω appears to constitute the main part of the epitope.

TABLE 9

Epitope and paratope of antibody C2595. Contact residues for all six complexes are shown. Residues numbering according to IFN-ω SEQ ID NO: 1 and IFN-α4a of SEQ ID NO: 19.

| Paratope | | Epitope | |
| --- | --- | --- | --- |
| IFNω/Fab357 | IFNα4A/Fab357 | IFNω | IFNα4A |
| VL: | | | G22 |
| H31 | H31 | R23 | R23 |
| N33 | N33 | I24 | I24 |
| Y37 | Y37 | S25 | S25 |
| N96 | N96 | P26 | H26 |
| L97 | L97 | F27 | F27 |
| L99 | L99 | | C29 |
| | | L30 | L30 |
| VH: | | K31 | K31 |
| I50 | I50 | R33 | R33 |
| T52 | | R34 | H34 |
| Y57 | Y57 | | V143 |
| T58 | T58 | M146 | A146 |
| Y59 | Y59 | E147 | E147 |
| | E101 | K150 | R150 |
| G103 | G103 | | |
| G104 | G104 | | |
| N105 | N105 | | |
| Y106 | Y106 | | |
| Y108 | Y108 | | |

All residues within 3.9 Å of the binding partners are considered contact residues. Antibody VL and VH residues are numbered sequentially.

Mode of Antibody Neutralization

C2595 neutralizes by blocking IFNAR2/IFN interactions.

Example 7. Epitope of M88 Derived from the Crystal Structure of Anti-IFNα Antibody M88 in Complex with IFNα4A The crystal structure of the anti-IFN antibody M88 in complex with IFNα4A was determined to 2.5 Å. The main epitope is the helical element A19-D35 of the AB loop of IFN. Binding of M88 will prevent IFNAR2 interactions. Thus, M88 is an IFNAR2 blocker. The structure sheds light on M88 binding cross-reactivity.

IFWM88 (hereafter M88 and FabM88 for mAb and Fab, respectively) is an antibody that neutralizes human IFNα. The M88 mAb shows binding to a number of IFNα subtypes, but little binding to human IFNω.

Materials and Methods

Proteins

The His-tagged FabM88 (IgG1/kappa isotype) was cloned and expressed in HEK293F cells and purified using affinity, and size-exclusion chromatography. The Fab was received in 20 mM Tris pH 7.4, 50 mM NaCl. IFNα4A was obtained from Crown Bioscience Inc. (in 20 mM Tris pH 7.4, 50 mM NaCl.

Crystallization of IFNα4A/FabM88 Complex

The complex was prepared by mixing of IFNα4A with FabM88 in molar ratio of 1.05:1.0 (excess IFNα4A), incubated at 4° C. for one hour, 20 fold diluted with 20 mM Tris pH 8.0, 10% glycerol, 0.1M NaCl, then concentrated to 9.25 mg/ml using Amicon-Ultra 10 kDa cutoff. Initial crystallization was set up with IH1, IH2 and PEGs suite (Qiagen). Crystallization of the complex was carried out by the vapor-diffusion method at 20° C. using an Oryx4 robot (Douglas Instruments). Crystals appeared from IH2#E12-25% PEG 3K, 0.2M ammonium citrate. These initial crystals were used to prepare crystallization seeds. To improve crystal quality, the IFNα4A/FabM88 complex was purified on Superdex™ 200 size exclusion chromatography media column (GE Healthcare) equilibrated with 20 mm MES pH 6.5, 0.1 M NaCl, 10% glycerol and concentrated to 8.16 mg/ml. Crystals suitable for X-diffraction were obtained from 28% PEG 3K, 0.2M ammonium citrate with MMS seeding as described (Obmolova et al., Acta Crystallogr D Biol Crystallogr 66:927-935, 2010).

X-Ray Data Collection and Structure Determination

For X-ray data collection, one crystal was soaked for a few seconds in the mother liquor supplemented with 20% glycerol, and flash frozen in the stream of nitrogen at 95 K. X-ray diffraction data were collected using a Rigaku Micro-Max™-007HF microfocus X-ray generator equipped with an Osmic™ VariMax™ confocal optics, Saturn 944 CCD detector, and an X-Stream™ 2000 cryocooling system (Rigaku, Tex.). Diffraction intensities were detected over a 235° crystal rotation in half-degree images. The X-ray data were processed with the program XDS. X-ray data statistics are given in Table 10.

The structure was solved by molecular replacement (MR) with Phaser. The search models for MR were the crystal structure of Fab 15 (PDB ID 3NCJ) and IFNα2 (PDB ID 1RH2, the Cα model of which was available in the PDB. To use for MR, the complete molecular model of IFNα2 was obtained by MR using Phaser with the Cα coordinates and reflection data in the PDB, and refined with PHENIX. The IFNα4A/FabM88 structure was refined using PHENIX and model adjustments were carried out using COOT. All other crystallographic calculations were performed with the CCP4 suite of programs. The elbow angle between the variable and constant domains was calculated with the program RBOW. All molecular graphics were generated with PyMol. The structure refinement statistics are given in Table 10.

TABLE 10

Crystal data and refinement statistics.

| Crystal data | |
| --- | --- |
| Space group | P1 |
| Unit cell dimensions | |
| a, b, c (Å) | 41.92, 84.71, 102.53 |
| α, β, γ (°) | 97.68, 90.12, 98.54 |
| Asymmetric unit content | 2 complexes |
| $V_m$ (Å$^3$/Da) | 2.62 |
| X-ray data | |
| Resolution (Å) | 50-2.5 (2.58-2.50) [a] |
| Number of measured reflections | 83,604 (1,217) |
| Number of unique reflections | 34,097 (588) |

TABLE 10-continued

Crystal data and refinement statistics.

| | |
|---|---|
| Completeness (%) | 72.1 (16.7) [b] |
| Redundancy | 2.5 (2.1) |
| R-merge | 0.43 (0.452) |
| <I/σ> | 18.0 (1.9) |
| B-factor (Wilson plot) (Å$^2$) | 43.8 |
| Refinement | |
| Resolution (Å) | 30.6-2.5 (2.58-2.50) |
| Number of refls used in refinement | 34,095 (640) |
| Completeness (%) | 72.2 |
| Number of all atoms | 8,844 |
| Number of water molecules | 149 |
| Rcryst (%) | 21.1 (42.8) |
| Rfree (%) | 27.3 (56.6) |
| RMSD bond lengths (Å) | 0.003 |
| RMSD bond angles (°) | 0.67 |
| RMSD B-factor main-chain (Å$^2$) | 6.6 |
| Mean B-factor (Å$^2$) | 47.4 |
| MolProbity [25] | |
| Clash score | 9.8 |
| Poor rotamers (%) | 3.9 |
| Ramachandran favored (%) | 94.4 |
| Ramachandran outliers (%) | 0.6 |
| Cβ deviation > 0.25 Å | 0 |

[a] Values for high-resolution shell are in parentheses.
[b] Low completeness because the highest resolution shells only contain the reflections in the corners of the detector.

Results
the Overall Structure

Figure 6:
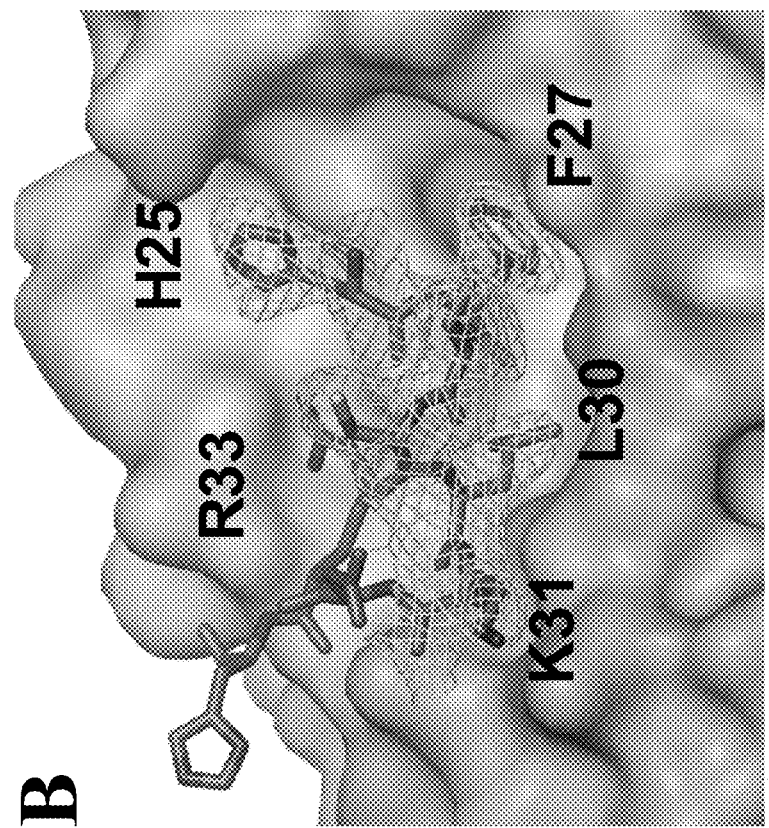
Figure 6:
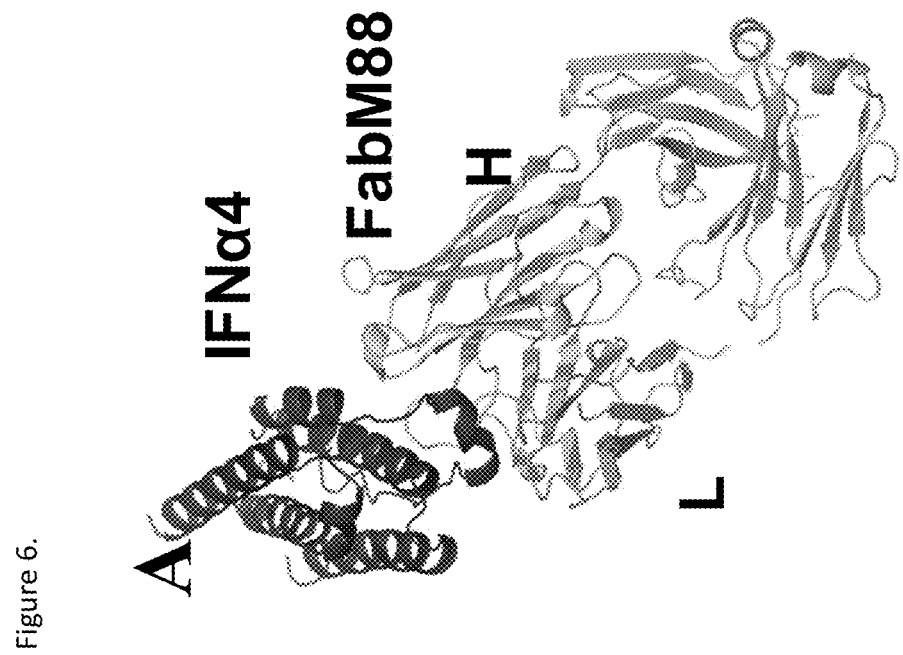

The overall molecular structure of the IFNα4A/FabM88 complex is shown in FIG. 6. There are two of these complexes in the asymmetric unit. The molecular models for the two independent IFNα4A molecules include residues 7-102 and 113-160 for one and 12-102 and 113-160 for the other. The connecting loop between residues 103 and 112 in both molecular is disordered. The two Fab molecules contain residues from 1 to 212 for the light chain and from 1 to 221 for the heavy chain. The C-terminal 6×His tag and inter-chain disulfide bond are disordered.

The two IFNα4A molecules have essentially identical conformation with an average rmsd of 0.132 Å for 122 Cα atoms. The two Fab molecules also have identical structures with an average rmsd of less than 0.5 Å for the entire Fab. Interestingly, the two Fabs have nearly identical elbow angles (172 and 174 degrees) according to RBOW.

IFNα Structure

Figure 7:
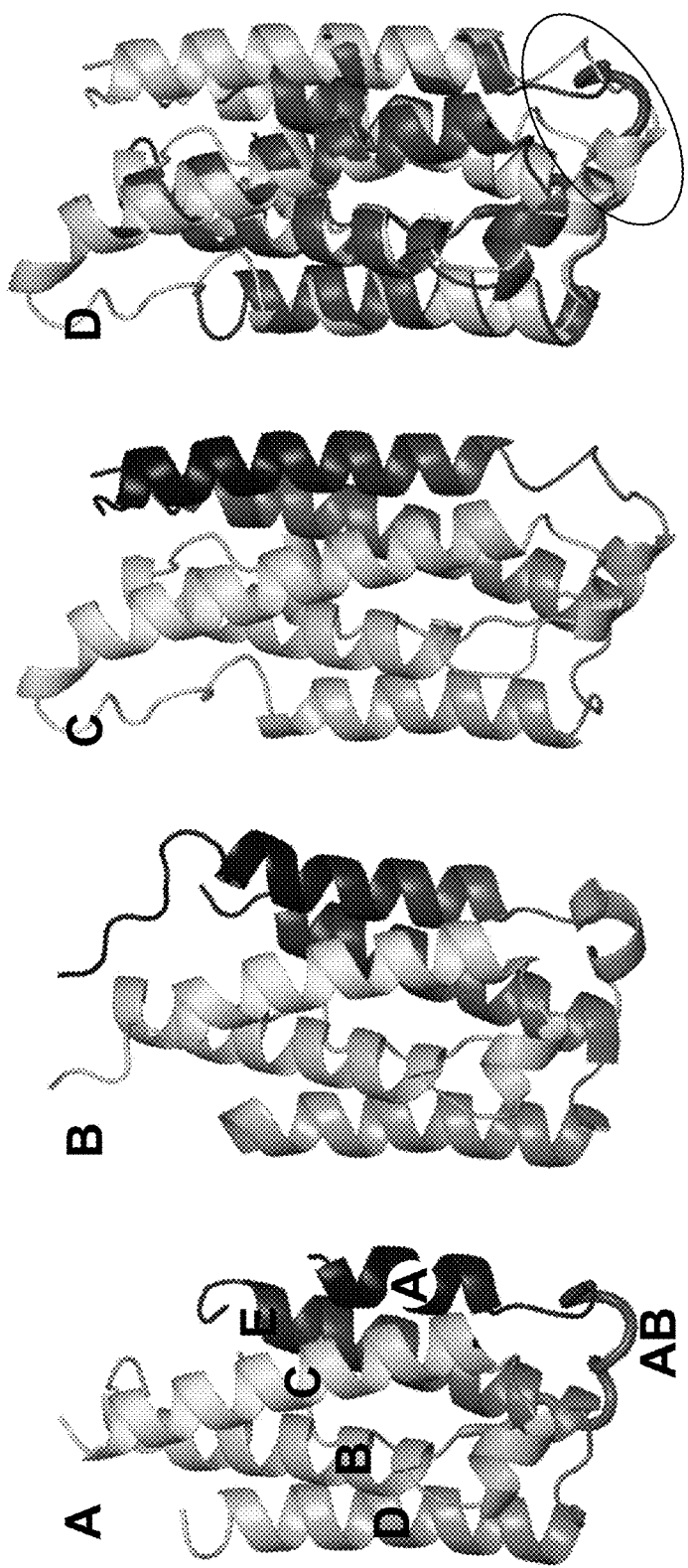

The molecular structure of IFNα4A (FIG. 7A) is very similar to IFNα2 with an average Cα rmsd of 0.5 to 0.7 Å. It is also very similar to IFNω (FIG. 7B, Cα rmsd of 0.61 Å for 112 residues) and IFNβ (FIG. 7C, Cα rmsd 0.85 Å for 94 residues). There are some significant differences between IFNα/ω and IFNβ due to one shorter residue in IFNβ AB loop (FIG. 7D).

the Epitope, Paratope and Ab/Ag Interactions

M88 recognizes a conformational epitope that is composed of residues of the AB loop (between A19 and D35) and residues V143, A146, E147 and R150 of helix E (Table 11). The paratope is composed of residues from all six CDRs. The paratope residues are mainly hydrophobic, which form a series of pockets into which dock the side chains of residues F27, L30, K31 and R33 of the short AB helix. The antibody and antigen interactions appear to be mostly vdw and hydrophobic packing. There are only a small number of H bonds between the antibody and antigen, and most of them involve backbone-backbone or sidechain-backbone interactions. Several residues F27, L30, K31 and R33 of the AB helix account for the majority of the Ab/Ag interactions. Thus, this region of IFNα4A constitutes the main part of the epitope. F50 of VL is not in direct contact with the antigen in the structure. But its sidechain is in the vicinity of Y32 (VL) and P105 (VH), which are involved in binding. Perhaps this residue was selected for its support of the CDR-H3 local structure to favor binding.

TABLE 11

Epitope and paratope of antibody M88.

| | PARATOPE | | EPITOPE | |
|---|---|---|---|---|
| | LHI | ABJ | LHI | ABJ |
| VL | | | IFNa4A | |
| | Y32 | Y32 | A19 | A19 |
| | S91 | S91 | H26 | |
| | Y92 | Y92 | F27 | F27 |
| | S93 | S93 | L30 | L30 |
| | T94 | T94 | K31 | K31 |
| | L96 | L96 | D32 | D32 |
| VH | | | R33 | R33 |
| | W47 | W47 | H34 | H34 |
| | G50 | G50 | D35 | D35 |
| | I51 | I51 | V143 | V143 |
| | I52 | | A146 | A146 |
| | F55 | F55 | E147 | E147 |
| | N59 | N59 | M149 | |
| | H99 | H99 | R150 | R150 |
| | L100 | L100 | S153 | |
| | G101 | G101 | | |
| | Y102 | Y102 | | |
| | A103 | A103 | | |
| | F104 | F104 | | |
| | P105 | P105 | | |
| | D106 | D106 | | |

All residues within 3.9 A of the binding partners are considered contact residues.
Antibody VL and VH residues are numbered sequentially. LHI and ABJ represent the two complexes.

Structure-Based Design of Libraries to Improve for Cross-Reactivity and Affinity M88 binds strongly a number of IFNα subtypes, but binds weakly to IFNω. Two strategies are possible based upon the current complex structure as well as molecular modeling using the IFNω structures. One strategy is to extend the CDR-L1 (extL1 library) by creating additional Ab/Ag interactions while maintaining all of the current contacts in the IFNα4A/M88 structure. Structural and sequence comparison show that a 5 residue surface patch (D32, H34, D35, Y130 and K134) is conserved 100% among all IFNα subtypes (Table 12).

TABLE 12

| | Residues 32-35 | | Residues 130-134 | |
|---|---|---|---|---|
| | Sequence | SEQ ID NO: | Sequence | SEQ ID NO: |
| IFNα | DRHD | 34 | YLxEK | 36 |
| IFNω | DRRD | 35 | YLKEK | 37 |

Four of these 5 residues are also conserved except R34 instead of H34 in IFNω. The CDR-L1 is distant from this well conserved surface patch. It is thus hypothesized that a longer CDR-L1, for example, that of germline IGKV4-1 (B3) which has an additional 6 residues in a 3-1-1 canonical structure, will be long enough to contact this patch. The longer CDR-L1 would provide additional interactions to all IFNα subtypes and IFNω, thus improving both affinity and broadening specificity. The sequence of the extended CDR-L1 can be optimized by phage display from a library. The design on the phage display library is shown in Table 13. Positions of extL1 facing away from the antigen are not randomized Position F50 of VL is the only non-human germline residue. Structurally it appears to provide support for CDR-L3. Thus, this position is also randomized to optimize its support of the extended CDR-L1.

TABLE 13

|  | Sequence | SEQ ID NO: |
|---|---|---|
| M88 | SQSIS SYL | 38 |
| M32 | SQSVLYSSNNKNYL | 39 |
| extL1 | SQSVLXSXXNXNYL | 40 |

X is any amino acid

Mode of Antibody Neutralization

Figure 8:
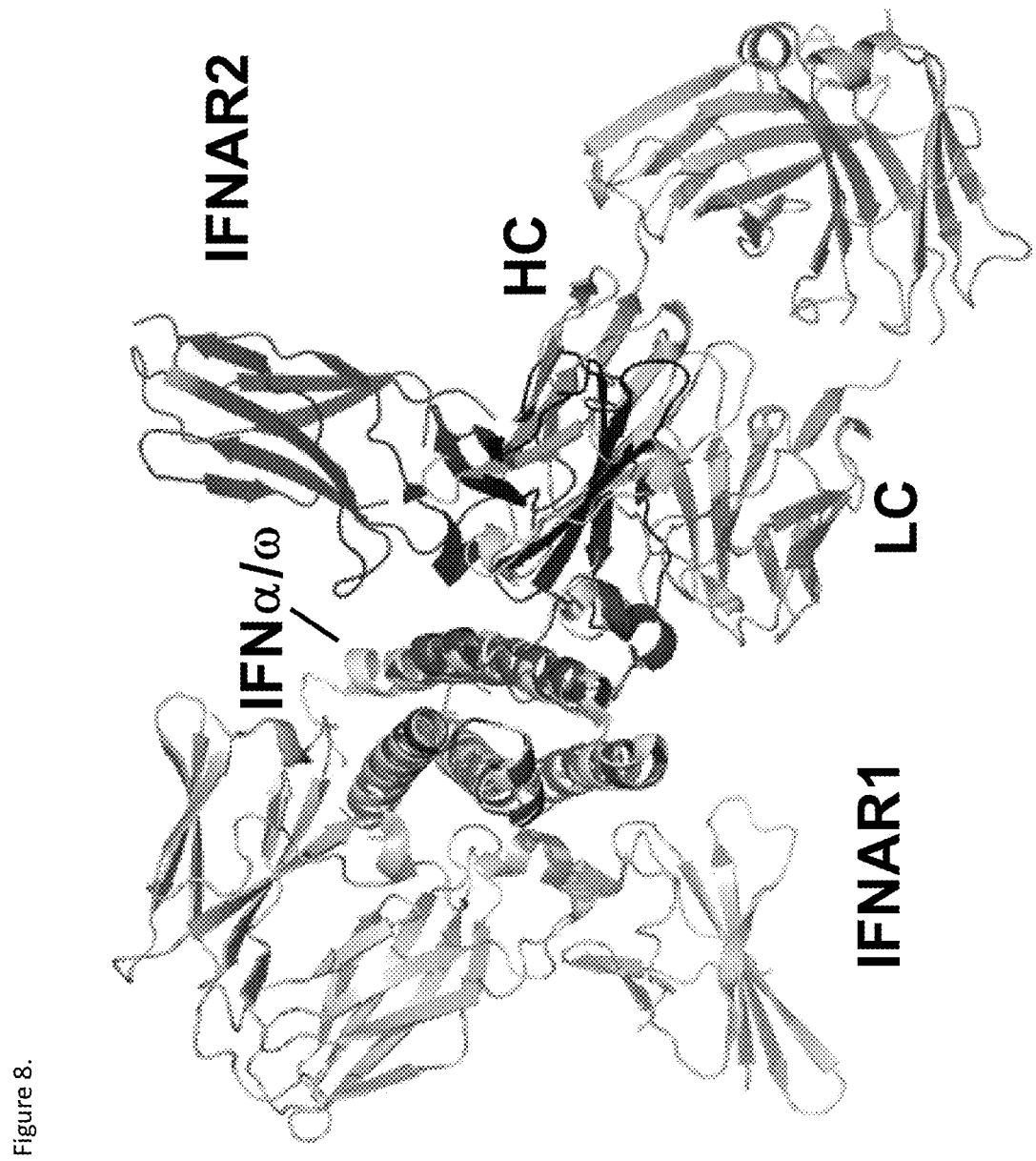

The crystal structure of IFNα/ω in complex with IFNAR1 and/or IFNAR2 has recently been reported (Thomas et al., Cell 146:621-632, 2011). FIG. 8 shows the overlay of M88/IFNα4 onto IFNω/IFNAR1/IFNA2 complex. It is clear that HC and IFNAR2 would overlap. Thus, M88 neutralizes by blocking IFNAR2/IFN interactions.

Example 8. Minimal Epitope on IFNα and IFNω Provides Broad IFNα/IFNω Neutralizing Activity The crystal structures of the IFNωT80E/FabM43, IFNα4A/FabM88, IFNα4A/Fab357 (c2595) and IFNω/Fab357 define a minimal common epitope required for broad neutralization of IFNω and multiple IFNα subtypes (Table 14). Analyses of the antibody/antigen interaction of the four crystal structures indicate that three residues in the AB loop in IFNα4a (SEQ ID NO: 19) and IFNω (SEQ ID NO: 1), F27, L30 and R33 form extensive contacts with the antibodies. These residues likely provide predominant contributions to antibody binding. Thus, F27, L30 and R33 are key elements of the IFNω/IFNα cross-neutralization epitope.

The conformational epitope is composed of residues from the AB loop (residues 22-34 of IFNω of SEQ ID NO:1 and of IFNα4a of SEQ ID NO: 19) with a short helical segment (27-29) and of residues in the helical E (134-154 is the helical E same residues for IFNω and all IFNα subtypes except IFNα2, which is 133-153). In particular, positions P26, F27, L30, K31, R33 and H34 of IFNω of SEQ ID NO:1 and residues H26, F27, L30, K31, R33 and H34 of IFNα4a of SEQ ID NO:19 are recognized by the neutralizing antibodies. These residues are largely conserved between various IFNα subtypes and IFNω, thus accounting for the cross-reactivity and differential specificity of these antibodies, although they come from different sources. Additional epitope residues are R22, R23, I24, S25, D32, D35, M149, K150 or L154 of IFNω and residues A19, G22, R23, I24, S25, H26, F27, C29, L30, K31, D32, R33, H34, D35, V143, A146, E147, M149, R150 or S153 of IFNα4a.

TABLE 14

| Epitopes | | | |
|---|---|---|---|
| M43 on IFN ω | M88 on IFNα4a | C2595 on IFNα4a | C2595 on IFNω |
| R22 | A19 | G22 | |
| | | R23 | R23 |
| | | I24 | I24 |
| | | S25 | S25 |
| P26 | H26 | H26 | P26 |
| F27 | F27 | F27 | F27 |
| | | C29 | |
| L30 | L30 | L30 | L30 |
| K31 | K31 | K31 | K31 |
| D32 | D32 | | |
| R33 | R33 | R33 | R33 |
| R34 | H34 | H34 | R34 |
| D35 | D35 | | |
| Q40 | | | |
| K134 | | | |
| | V143 | V143 | |
| M146 | A146 | A146 | M146 |
| | E147 | E147 | E147 |
| M149 | M149 | | |
| K150 | R150 | R150 | K150 |
| F153 | S153 | | |
| L154 | | | |

We claim:

1. An isolated monoclonal antibody that binds human interferon omega (IFNω) at least at residues F27, L30 and R33 of SEQ ID NO: 1, wherein the antibody neutralizes an activity of IFNω, IFNαB2, IFNαC, IFNαF, IFNαG and IFNαJ1 and comprises a heavy chain variable region (VH) amino acid sequence of SEQ ID NO: 23 or SEQ ID NO:27 and a light chain variable region (VL) amino acid sequence of SEQ ID NO: 24 or SEQ ID NO: 28.

2. A composition comprising the antibody of claim 1 and a pharmaceutically acceptable carrier.

3. The antibody of claim 1, wherein the antibody does not bind or neutralize human IFNα D.

4. The antibody of claim 1, wherein the antibody neutralizes the activity of IFNα A, IFNα H2, IFNα K, IFNα WA and IFNα 4a.

5. The antibody of claim 4, wherein the activity is inhibition of secreted embryonic alkaline phosphatase (SEAP) expression under the interferon inducible ISG54 promoter in HEK293 cells stably expressing signal transducer and activator of transcription 2 (STAT2), interferon regulatory factor 9 (IRF9) and SEAP.

6. The antibody of claim 5, wherein the antibody neutralizes the activity of IFNω with an $IC_{50}$ value of between about $0.9 \times 10^{-9}$ M and about $1.85 \times 10^{-8}$ M.

7. The antibody of claim 6, wherein the antibody binds IFNω with a dissociation constant ($K_D$) of between about $0.3 \times 10^{-9}$ M and about $4.5 \times 10^{-9}$ M, wherein the $K_D$ is measured using SPR technology with ProteOn (Bio-Rad Hercules, Calif.), with antibody loaded on an antibody coupled chip for 2 minutes at a flow rate of 30 μl/min, washing with running buffer for 2 minutes at a flow rate of 50 μl/ml, and associating recombinant IFN proteins at 5 different concentrations ranging from 100 nM to 1.23 nM with 1:3 dilution were for 3 minutes and dissociating for 10 minutes, both at the flow rate of 50 μl/ml.

8. The antibody of claim 4, wherein the antibody inhibits an activity of viral-induced leukocyte interferon, wherein the activity of viral-induced leukocyte interferon is IP-10 release in whole blood induced by 100 U/ml of interferon.

9. The antibody of claim 8, wherein the activity is inhibited by more than 50% in the presence of 50 μg/ml antibody.

10. The antibody of claim 4, wherein the antibody does not bind or neutralize human interferon-β (IFNβ).

11. The antibody of claim 4, wherein the antibody is human, humanized or human-adapted.

12. The antibody of claim 11, wherein the antibody is of IgG1, IgG2, IgG3 or IgG4 isotype.

13. The antibody of claim 11, wherein the antibody is bispecific.

14. The antibody of claim 13, wherein the antibody binds BLyS, CD40L, IL-6, CD27, BDCA2 or the p40 subunit of IL-12 or IL-23.

15. A composition comprising the antibody of claim 14 and a pharmaceutically acceptable carrier.

* * * * *